US008506485B2

(12) United States Patent
Deckman et al.

(10) Patent No.: US 8,506,485 B2
(45) Date of Patent: *Aug. 13, 2013

(54) DEVICES AND METHODS FOR TREATMENT OF TISSUE

(75) Inventors: Robert K. Deckman, San Bruno, CA (US); Craig Gerbi, Mountain View, CA (US); Michael Munrow, Belmont, CA (US); Jessica Grossman, San Francisco, CA (US)

(73) Assignee: Gynesonics, Inc, Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/973,587

(22) Filed: Dec. 20, 2010

(65) Prior Publication Data

US 2011/0288412 A1    Nov. 24, 2011

Related U.S. Application Data

(63) Continuation of application No. 11/564,164, filed on Nov. 28, 2006, now Pat. No. 7,874,986, which is a continuation-in-part of application No. 11/409,496, filed on Apr. 20, 2006, now Pat. No. 7,815,571.

(51) Int. Cl.
*A61B 8/08* (2006.01)
*A61H 1/00* (2006.01)
*A61B 18/18* (2006.01)

(52) U.S. Cl.
USPC ............... 600/439; 600/437; 601/2; 606/41; 606/46

(58) Field of Classification Search
None
See application file for complete search history.

(56) References Cited

U.S. PATENT DOCUMENTS

| 4,289,132 A | 9/1981 | Rieman |
| 4,802,487 A | 2/1989 | Martin et al. |
| 4,936,281 A | 6/1990 | Stasz |
| 5,000,185 A | 3/1991 | Yock |
| 5,372,138 A | 12/1994 | Crowley et al. |
| 5,372,587 A | 12/1994 | Hammerslag et al. |
| 5,456,689 A | 10/1995 | Kresch |
| 5,471,988 A | 12/1995 | Fujio et al. |

(Continued)

FOREIGN PATENT DOCUMENTS

| WO | WO 97/17105 | 5/1997 |
| WO | WO 98/11834 | 3/1998 |

(Continued)

OTHER PUBLICATIONS

International search report and written opinion dated Nov. 13, 2007 for PCT/US2007/066235.

(Continued)

*Primary Examiner* — Long V. Le
*Assistant Examiner* — Angela M Hoffa
(74) *Attorney, Agent, or Firm* — Wilson, Sonsini, Goodrich & Rosati

(57) ABSTRACT

Delivery systems, and methods using the same, having an ultrasound viewing window for improved imaging and a needle for ablation treatment of target tissues. In an embodiment, the target tissue is a fibroid within a female's uterus. In an embodiment, the delivery system includes a rigid shaft having a proximal end, a distal end, and an axial passage extending through the rigid shaft. In an embodiment, the axial passage is configured for removably receiving the ultrasound imaging insert having an ultrasound array disposed a distal portion.

9 Claims, 22 Drawing Sheets

(56) References Cited

U.S. PATENT DOCUMENTS

| | | | |
|---|---|---|---|
| 5,492,126 | A | 2/1996 | Hennige et al. |
| 5,527,331 | A | 6/1996 | Kresch et al. |
| 5,531,676 | A | 7/1996 | Edwards et al. |
| 5,649,911 | A | 7/1997 | Trerotola |
| 5,666,954 | A | 9/1997 | Chapelon et al. |
| 5,697,897 | A | 12/1997 | Buchholtz et al. |
| 5,730,752 | A | 3/1998 | Alden et al. |
| 5,741,287 | A | 4/1998 | Alden et al. |
| 5,769,880 | A | 6/1998 | Truckai et al. |
| 5,842,994 | A | 12/1998 | TenHoff et al. |
| 5,853,368 | A | 12/1998 | Solomon et al. |
| 5,860,974 | A | 1/1999 | Abele |
| 5,863,294 | A | 1/1999 | Alden |
| 5,873,828 | A | 2/1999 | Fujio et al. |
| 5,876,340 | A | 3/1999 | Tu et al. |
| 5,876,399 | A | 3/1999 | Chia et al. |
| 5,891,137 | A | 4/1999 | Chia et al. |
| 5,906,615 | A | 5/1999 | Thompson |
| 5,916,198 | A | 6/1999 | Dillow |
| 5,957,941 | A | 9/1999 | Ream |
| 5,964,740 | A | 10/1999 | Ouchi |
| 5,979,452 | A | 11/1999 | Fogarty et al. |
| 5,979,453 | A | 11/1999 | Savage et al. |
| 5,984,942 | A | 11/1999 | Alden et al. |
| 6,002,968 | A | 12/1999 | Edwards |
| 6,007,499 | A | 12/1999 | Martin et al. |
| 6,032,673 | A | 3/2000 | Savage et al. |
| 6,039,748 | A | 3/2000 | Savage et al. |
| 6,059,766 | A | 5/2000 | Greff |
| 6,077,257 | A | 6/2000 | Edwards et al. |
| 6,141,577 | A | 10/2000 | Rolland et al. |
| 6,146,378 | A | 11/2000 | Mikus et al. |
| 6,146,380 | A | 11/2000 | Racz et al. |
| 6,158,250 | A | 12/2000 | Tibbals, Jr. et al. |
| 6,171,249 | B1 | 1/2001 | Chin et al. |
| 6,190,383 | B1 | 2/2001 | Schmaltz et al. |
| 6,193,714 | B1 | 2/2001 | McGaffigan et al. |
| 6,211,153 | B1 | 4/2001 | Garnick et al. |
| 6,238,336 | B1 | 5/2001 | Ouchi |
| 6,254,601 | B1 | 7/2001 | Burbank et al. |
| 6,280,441 | B1 | 8/2001 | Ryan |
| 6,296,639 | B1 | 10/2001 | Truckai et al. |
| 6,306,129 | B1 | 10/2001 | Little et al. |
| 6,315,741 | B1 | 11/2001 | Martin et al. |
| 6,379,348 | B1 | 4/2002 | Onik |
| 6,405,732 | B1 | 6/2002 | Edwards et al. |
| 6,419,648 | B1 | 7/2002 | Vitek et al. |
| 6,419,653 | B2 | 7/2002 | Edwards et al. |
| 6,419,673 | B1 | 7/2002 | Edwards et al. |
| 6,425,867 | B1 | 7/2002 | Vaezy et al. |
| 6,432,067 | B1 | 8/2002 | Martin et al. |
| 6,447,477 | B2 | 9/2002 | Burney et al. |
| 6,463,331 | B1 | 10/2002 | Edwards |
| 6,482,203 | B2 | 11/2002 | Paddock et al. |
| 6,485,413 | B1 | 11/2002 | Boppart et al. |
| 6,506,154 | B1 | 1/2003 | Ezion et al. |
| 6,506,156 | B1 | 1/2003 | Jones et al. |
| 6,506,171 | B1 | 1/2003 | Vitek et al. |
| 6,507,747 | B1 | 1/2003 | Gowda et al. |
| 6,508,815 | B1 | 1/2003 | Strul et al. |
| 6,522,142 | B1 | 2/2003 | Freundlich |
| 6,526,320 | B2 | 2/2003 | Mitchell |
| 6,540,677 | B1 | 4/2003 | Angelsen et al. |
| 6,543,272 | B1 | 4/2003 | Vitek |
| 6,550,482 | B1 | 4/2003 | Burbank et al. |
| 6,554,780 | B1 | 4/2003 | Sampson et al. |
| 6,559,644 | B2 | 5/2003 | Froundlich et al. |
| 6,569,159 | B1 | 5/2003 | Edwards et al. |
| 6,572,613 | B1 | 6/2003 | Ellman et al. |
| 6,589,237 | B2 | 7/2003 | Woloszko et al. |
| 6,592,559 | B1 | 7/2003 | Pakter et al. |
| 6,602,251 | B2 | 8/2003 | Burbank et al. |
| 6,610,054 | B1 | 8/2003 | Edwards et al. |
| 6,612,988 | B2 | 9/2003 | Maor et al. |
| 6,613,004 | B1 | 9/2003 | Vitek et al. |
| 6,613,005 | B1 | 9/2003 | Friedman et al. |
| 6,623,481 | B1 | 9/2003 | Garbagnati et al. |
| 6,626,854 | B2 | 9/2003 | Friedman et al. |
| 6,626,855 | B1 | 9/2003 | Weng et al. |
| 6,632,193 | B1 | 10/2003 | Davison et al. |
| 6,635,055 | B1 | 10/2003 | Cronin |
| 6,635,065 | B2 | 10/2003 | Burbank et al. |
| 6,638,275 | B1 | 10/2003 | McGaffigan |
| 6,638,286 | B1 | 10/2003 | Burbank et al. |
| 6,645,162 | B2 | 11/2003 | Friedman et al. |
| 6,645,202 | B1 | 11/2003 | Pless et al. |
| 6,652,516 | B1 | 11/2003 | Gough |
| 6,660,002 | B1 | 12/2003 | Edwards et al. |
| 6,660,024 | B1 | 12/2003 | Flaherty et al. |
| 6,663,624 | B2 | 12/2003 | Edwards et al. |
| 6,663,626 | B2 | 12/2003 | Truckai et al. |
| 6,666,833 | B1 | 12/2003 | Friedman et al. |
| 6,679,855 | B2 | 1/2004 | Horn et al. |
| 6,685,639 | B1 | 2/2004 | Wang et al. |
| 6,689,128 | B2 | 2/2004 | Sliwa, Jr. et al. |
| 6,692,490 | B1 | 2/2004 | Edwards |
| 6,701,931 | B2 | 3/2004 | Sliwa, Jr. et al. |
| 6,705,994 | B2 | 3/2004 | Vortman et al. |
| 6,712,815 | B2 | 3/2004 | Sampson et al. |
| 6,716,184 | B2 | 4/2004 | Vaezy et al. |
| 6,719,755 | B2 | 4/2004 | Sliwa, Jr. et al. |
| 6,728,571 | B1 | 4/2004 | Barbato |
| 6,730,081 | B1 | 5/2004 | Desai |
| 6,735,461 | B2 | 5/2004 | Vitek et al. |
| 6,743,184 | B2 | 6/2004 | Sampson et al. |
| 6,746,447 | B2 | 6/2004 | Davison et al. |
| 6,764,488 | B1 | 7/2004 | Burbank et al. |
| 6,773,431 | B2 | 8/2004 | Eggers et al. |
| 6,790,180 | B2 | 9/2004 | Vitek |
| 6,805,128 | B1 | 10/2004 | Pless et al. |
| 6,805,129 | B1 | 10/2004 | Pless et al. |
| 6,813,520 | B2 | 11/2004 | Truckai et al. |
| 6,832,996 | B2 | 12/2004 | Woloszko et al. |
| 6,837,887 | B2 | 1/2005 | Woloszko et al. |
| 6,837,888 | B2 | 1/2005 | Ciarrocca et al. |
| 6,840,935 | B2 | 1/2005 | Lee |
| 6,936,048 | B2 | 8/2005 | Hurst |
| 6,994,706 | B2 | 2/2006 | Chornenky et al. |
| 7,331,957 | B2 | 2/2008 | Woloszko et al. |
| 7,517,346 | B2 | 4/2009 | Sloan et al. |
| 7,549,424 | B2 | 6/2009 | Desai et al. |
| 7,771,357 | B2 * | 8/2010 | Burbank et al. ............ 600/439 |
| 7,815,571 | B2 | 10/2010 | Deckman et al. |
| 7,824,398 | B2 | 11/2010 | Woloszko et al. |
| 7,874,986 | B2 * | 1/2011 | Deckman et al. ............ 600/439 |
| 7,918,795 | B2 * | 4/2011 | Grossman ............ 600/439 |
| 8,088,072 | B2 * | 1/2012 | Munrow et al. ............ 600/464 |
| 2001/0014805 | A1 | 8/2001 | Burbank et al. |
| 2001/0051802 | A1 | 12/2001 | Woloszko et al. |
| 2002/0002393 | A1 | 1/2002 | Mitchell |
| 2002/0022835 | A1 | 2/2002 | Lee |
| 2002/0052600 | A1 | 5/2002 | Davison et al. |
| 2002/0068871 | A1 | 6/2002 | Mendlein et al. |
| 2002/0077550 | A1 | 6/2002 | Rabiner et al. |
| 2002/0183735 | A1 | 12/2002 | Edwards et al. |
| 2003/0009164 | A1 | 1/2003 | Woloszko et al. |
| 2003/0014046 | A1 | 1/2003 | Edwards |
| 2003/0028111 | A1 | 2/2003 | Vaezy et al. |
| 2003/0032896 | A1 | 2/2003 | Bosley et al. |
| 2003/0130575 | A1 | 7/2003 | Desai et al. |
| 2003/0130655 | A1 | 7/2003 | Woloszko et al. |
| 2003/0195420 | A1 | 10/2003 | Mendlein et al. |
| 2003/0195496 | A1 | 10/2003 | Maguire et al. |
| 2003/0199472 | A1 | 10/2003 | Al-Hendy et al. |
| 2003/0216725 | A1 | 11/2003 | Woloszko et al. |
| 2003/0216759 | A1 | 11/2003 | Burbank et al. |
| 2004/0002699 | A1 | 1/2004 | Ryan et al. |
| 2004/0006336 | A1 | 1/2004 | Swanson |
| 2004/0030268 | A1 | 2/2004 | Weng et al. |
| 2004/0054366 | A1 | 3/2004 | Davison et al. |
| 2004/0120668 | A1 | 6/2004 | Loeb |
| 2004/0143252 | A1 | 7/2004 | Hurst |
| 2004/0153057 | A1 | 8/2004 | Davison |
| 2004/0175399 | A1 | 9/2004 | Schiffman |

| | | | |
|---|---|---|---|
| 2004/0176760 A1 | 9/2004 | Qiu | |
| 2004/0193028 A1 | 9/2004 | Jones et al. | |
| 2004/0215182 A1 | 10/2004 | Lee | |
| 2004/0230190 A1 | 11/2004 | Dahla et al. | |
| 2004/0254572 A1 | 12/2004 | McIntyre et al. | |
| 2005/0038340 A1 | 2/2005 | Vaezy et al. | |
| 2005/0085730 A1 | 4/2005 | Flesch et al. | |
| 2005/0107781 A1 | 5/2005 | Ostrovsky et al. | |
| 2005/0124882 A1 | 6/2005 | Ladabaum et al. | |
| 2005/0149013 A1 | 7/2005 | Lee | |
| 2005/0177209 A1 | 8/2005 | Leung et al. | |
| 2005/0197577 A1 | 9/2005 | Makin et al. | |
| 2005/0215990 A1 | 9/2005 | Govari | |
| 2005/0216039 A1 | 9/2005 | Lederman | |
| 2005/0228288 A1 | 10/2005 | Hurst | |
| 2005/0255039 A1 | 11/2005 | Desai | |
| 2005/0256405 A1 | 11/2005 | Makin et al. | |
| 2006/0010207 A1 | 1/2006 | Akerman et al. | |
| 2006/0058680 A1* | 3/2006 | Solomon | 600/466 |
| 2006/0178665 A1 | 8/2006 | Sloan | |
| 2006/0189972 A1 | 8/2006 | Grossman | |
| 2006/0241368 A1 | 10/2006 | Fichtinger et al. | |
| 2007/0006215 A1 | 1/2007 | Epstein et al. | |
| 2007/0161905 A1* | 7/2007 | Munrow | 600/459 |
| 2007/0249936 A1 | 10/2007 | Deckman et al. | |
| 2007/0249939 A1* | 10/2007 | Gerbi et al. | 600/462 |
| 2008/0033493 A1* | 2/2008 | Deckman et al. | 607/3 |
| 2009/0131790 A1* | 5/2009 | Munrow et al. | 600/439 |
| 2009/0287081 A1* | 11/2009 | Grossman et al. | 600/439 |
| 2010/0056926 A1* | 3/2010 | Deckman et al. | 600/461 |
| 2011/0087100 A1* | 4/2011 | Grossman | 600/439 |
| 2012/0035474 A1* | 2/2012 | Deckman et al. | 600/439 |
| 2012/0078134 A1* | 3/2012 | Munrow et al. | 600/567 |
| 2012/0316440 A1* | 12/2012 | Munrow et al. | 600/439 |

FOREIGN PATENT DOCUMENTS

| | | |
|---|---|---|
| WO | WO 98/14169 | 4/1998 |
| WO | WO 99/43366 | 9/1999 |
| WO | WO 00/00098 | 1/2000 |
| WO | WO 01/80723 A2 | 11/2001 |
| WO | WO 01/95819 A1 | 12/2001 |
| WO | WO 02/11639 A1 | 2/2002 |
| WO | WO 03/005882 A2 | 1/2003 |
| WO | WO 03/005882 A3 | 1/2003 |
| WO | WO 03/065908 A1 | 8/2003 |
| WO | WO 03/088833 A1 | 10/2003 |
| WO | WO 2004/002293 A2 | 1/2004 |
| WO | WO 2004/002550 A2 | 1/2004 |
| WO | WO 2004/020011 A1 | 3/2004 |
| WO | WO 2004/035110 A2 | 4/2004 |
| WO | WO 2004/058328 A2 | 7/2004 |
| WO | WO 2004/064658 | 8/2004 |

OTHER PUBLICATIONS

Alterovitz et al., "Simulating Needle Insertion and Radioactive Seed Implantation for Prostate Brachytherapy," Medicine Meets Virtual Reality 11, Westwood et al. (Eds.), IOS Press, Jan. 2003, pp. 19-25.

Bergamini et al., "Laparoscopic Radiofrequency Thermal Ablation: A New Approach to Symptomatic Uterine Myomas," Am. J. Obstetrics and Gynecology (2005) 192: 768-73.

CNN.com Health Women, "Experimental technique uses lasers to shrink uterine fibroids," Nov. 28, 2000.

Hindley et al.; "MRI guidance of focused ultrasound therapy of uterine fibroids: Early results," American Journal of Roentgenology, 2004, 183(6): 1173-1719.

Kanaoka et al., "Microwave endometrial ablation at a frequency of 2.45 Ghz. A pilot study," J Reprod Med. Jun. 2001; 46(60): 559-63.

Law et al., "Magnetic resonance-guided percutaneous laser ablation of uterine fibroids," J Magn Reson Imaging, Oct. 2000; 12(4):565-70.

Liu et al., "Catheter-Based Intraluminal Sonography," J. Ultrasound Med., 2004, 23:145-160.

Mogami et al., "Usefulness of MR-guided percutaneous cryotherapy," Med. Imaging Technol. 2004, 22(3): 131-6. (English abstract).

Okamura et al., "Force Modeling for Needle Insertion into Soft Tissue," IEEE Transactions on Biomedical Engineering, Oct. 2001, 10 (51): 1707-1716.

RSNA 2000 Explore News Release; "Lasers Liquefy Uterine Fibroid Tumors," 11:30 a.m. CST, Monday, Nov. 27, 2000.

Senoh et al., "Saline Infusion Contrast Intrauterine Sonographic Assessment of the Endometrium with High-Frequency, Real-Time Miniature Transducer Normal Menstrual Cycle: a Preliminary Report," Human Reproduction, 14 (10): 2600-2603, 1999.

Vascular and Interventional Radiology, SRSC; "Nonsurgical Treatment of Uterine Fibroids", retrieved from the Internet: <http://drfibroid.com/treatment.htm>, 2005, 2 pages total.

Websand, Inc., New treatment options for fibroid tumors, Copyright 2002 by WebSand, Inc.

Extended European Search Report and Opinion of European Patent Application No. 07760319.9, mailed Nov. 23, 2010, 7 pages total.

U.S. Appl. No. 13/667,891, filed Nov. 2, 2012, Deckman et al.

MSNBC OnLine Articles, About Us: Articles; "Intrauerine Fibroids Can Now Be Treated Nonsurgically" http://www.fibroids.com/news-blog/2004/08/intrauterine-fibroids-can-now-be-treated-nonsurgically/ Aug. 23, 2004.

* cited by examiner

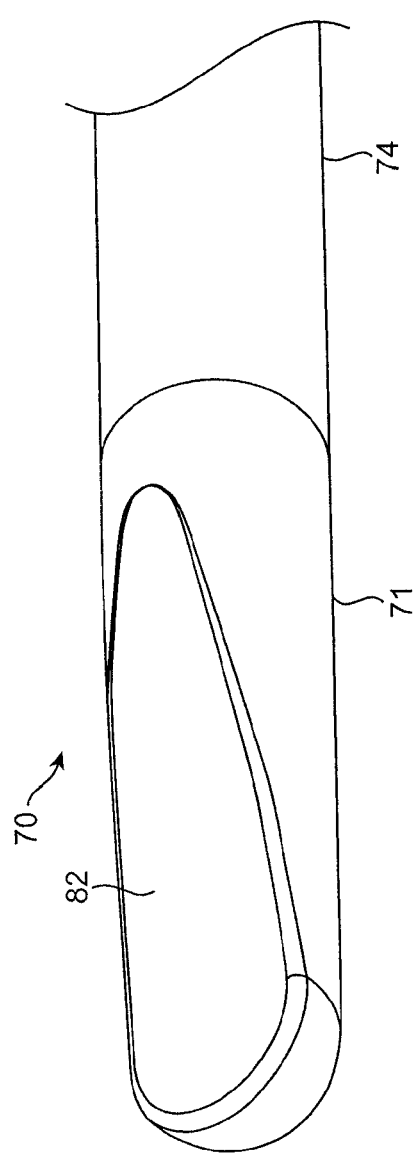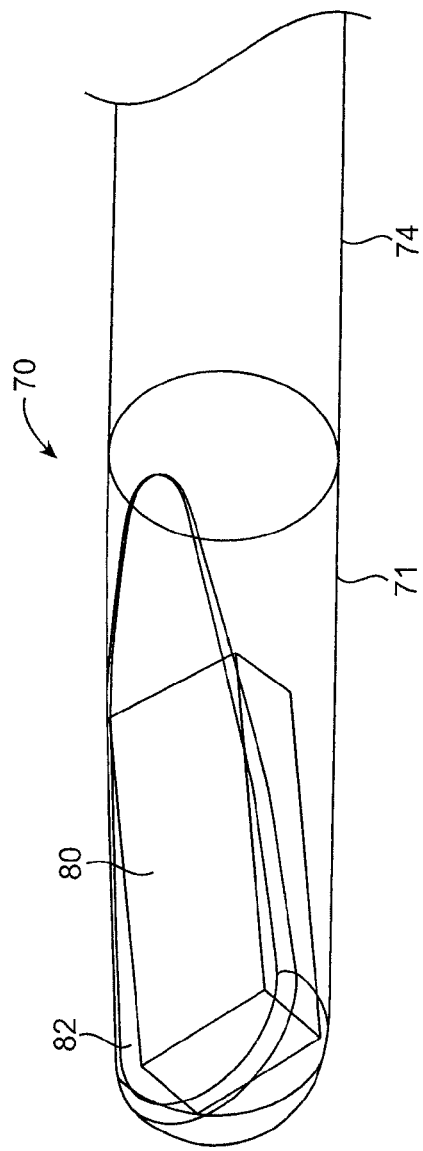

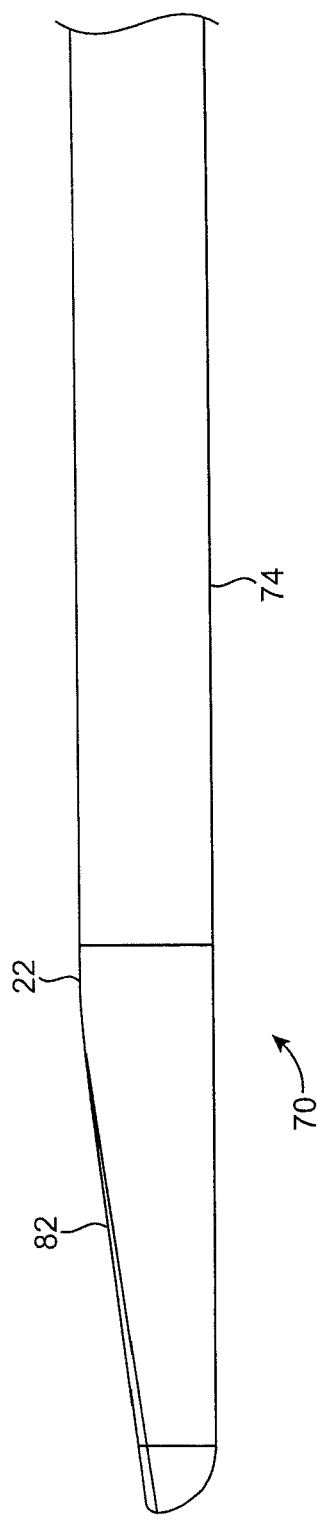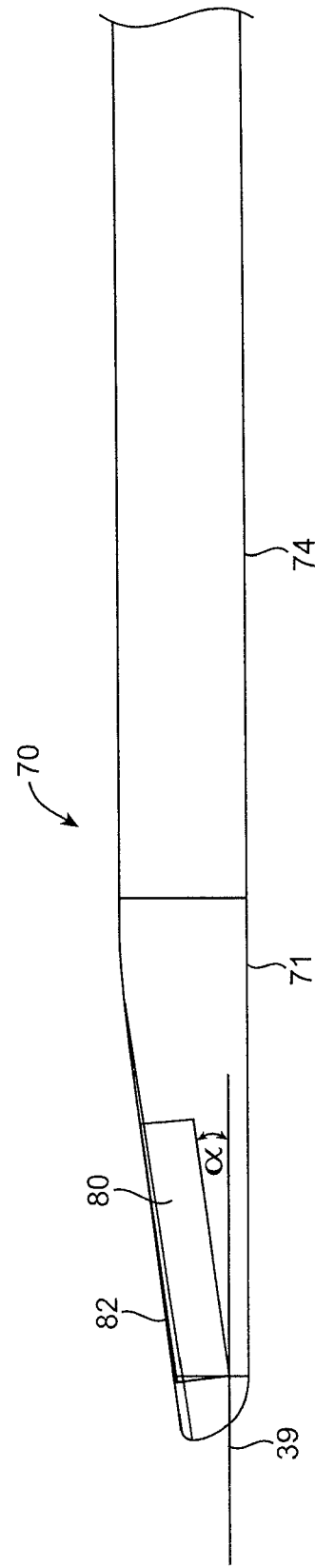

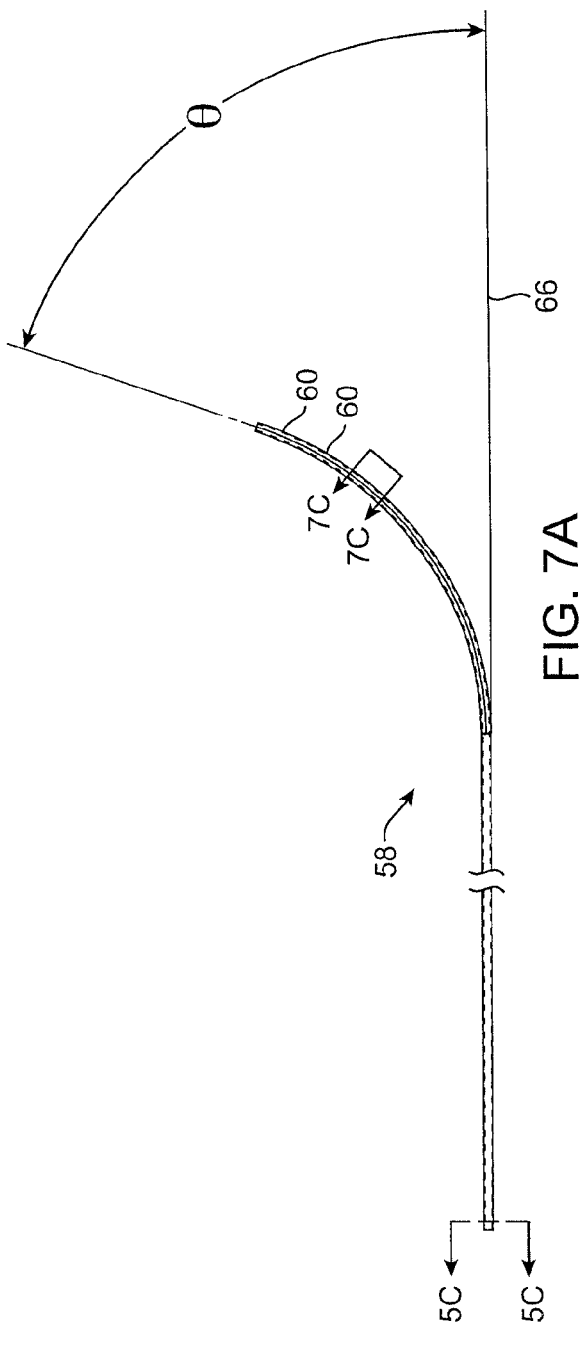
FIG. 7A
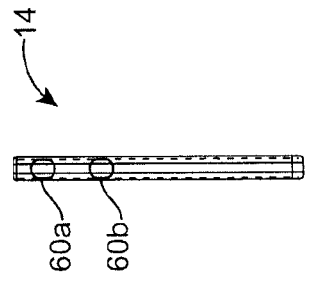
FIG. 7D
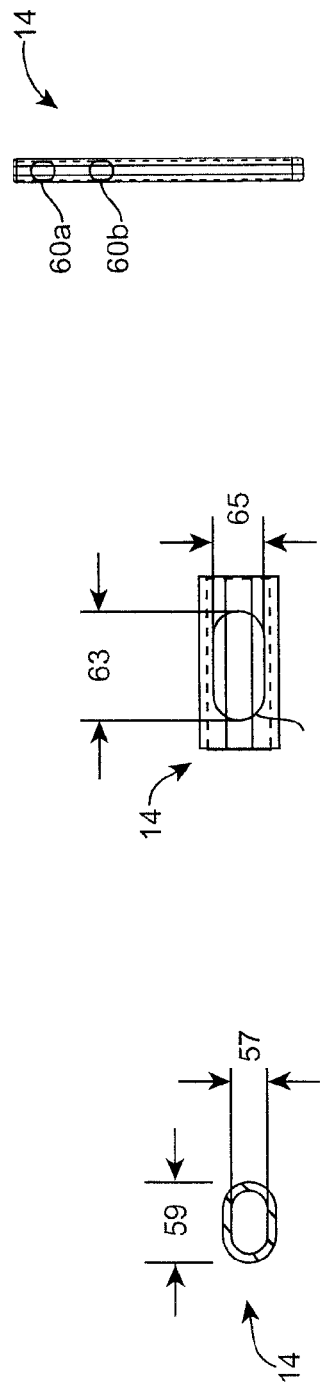
FIG. 7B
FIG. 7C

DEVICES AND METHODS FOR TREATMENT OF TISSUE

CROSS-REFERENCE TO RELATED APPLICATIONS

This application is a continuation of application Ser. No. 11/564,164, filed on Nov. 28, 2006, which was a continuation-in-part of application Ser. No. 11/409,496, filed on Apr. 20, 2006, the full disclosures of which are incorporated herein by reference.

FIELD OF INVENTION

The present invention relates generally to medical systems and methods. More particularly, the invention relates to delivery systems having an ultrasound probe for improved imaging and a curved needle for ablation treatment, and methods for using the same.

BACKGROUND OF THE INVENTION

Treatment of the female reproductive tract and other conditions of dysfunctional uterine bleeding and fibroids remain with unmet clinical needs. Fibroids are benign tumors of the uterine myometria (muscle) and are the most common tumor of the female pelvis. Fibroid tumors affect up to 30% of women of childbearing age and can cause significant symptoms such as discomfort, pelvic pain, mennorhagia, pressure, anemia, compression, infertility, and miscarriage. Fibroids may be located in the myometrium (intramural), adjacent the endometrium (submucosal), or in the outer layer of the uterus (subserosal). Most common fibroids are a smooth muscle overgrowth that arise intramurally and can grow to be several centimeters in diameter.

Current treatments for fibroids include either or both pharmacological therapies and surgical interventions. Pharmacological treatments include the administration of medications such as NSAIDS, estrogen-progesterone combinations, and GnRH analogues. All medications are relatively ineffective and are palliative rather than curative.

Surgical interventions include hysterectomy (surgical removal of the uterus) and myomectomy. Surgical myomectomy, in which fibroids are removed, is an open surgical procedure requiring laparotomy and general anesthesia. Often these surgical procedures are associated with the typical surgical risks and complications along with significant blood loss and can only remove a portion of the culprit tissue.

To overcome at least some of the problems associated with open surgical procedures, laparoscopic myomectomy was pioneered in the early 1990's. However, laparoscopic myomectomy remains technically challenging, requiring laparoscopic suturing, limiting its performance to only the most skilled of laparoscopic gynecologists. Other minimally invasive treatments for uterine fibroids include hysteroscopy, uterine artery ablation, endometrial ablation, and myolysis.

While effective, hysterectomy has many undesirable side effects such as loss of fertility, open surgery, sexual dysfunction, and long recovery time. There is also significant morbidity (sepsis, hemorrhage, peritonitis, bowel and bladder injury), mortality and cost associated with hysterectomy. Hysteroscopy is the process by which a thin fiber optic camera is used to image inside the uterus and an attachment may be used to destroy tissue. Hysteroscopic resection is a surgical technique that uses a variety of devices (loops, roller balls, bipolar electrodes) to ablate or resect uterine tissue. The procedure requires the filling of the uterus with fluid for better viewing, and thus has potential side effects of fluid overload. Hysteroscopic ablation is limited by its visualization technique and thus, only appropriate for fibroids which are submucosal and/or protrude into the uterine cavity.

Uterine artery embolization was introduced in the early 1990's and is performed through a groin incision by injecting small particles into the uterine artery to selectively block the blood supply to fibroids and refract its tissue. Complications include pelvic infection, premature menopause and severe pelvic pain. In addition, long term MRI data suggests that incomplete fibroid infarction may result in regrowth of infarcted fibroid tissue and symptomatic recurrence.

Endometrial ablation is a procedure primarily used for dysfunctional (or abnormal) uterine bleeding and may be used, at times, for management of fibroids. Endometrial ablation relies on various energy sources such as cryo, microwave and radiofrequency energy. Endometrial ablation destroys the endometrial tissue lining the uterus, and although an excellent choice for treatment of dysfunctional uterine bleeding, it does not specifically treat fibroids. This technique is also not suitable treatment of women desiring future childbearing.

Myolysis was first performed in the 1980's using lasers or radio frequency (RF) energy to coagulate tissue, denature proteins, and necrose myometrium using laparoscopic visualization. Laparoscopic myolysis can be an alternative to myomectomy, as the fibroids are coagulated and then undergo coagulative necrosis resulting in a dramatic decrease in size. As with all laparoscopic techniques, myolysis treatment is limited by the fact that it can only allow for visualization of subserosal fibroids.

Needle myolysis uses a laparoscope, percutaneous, or open technique to introduce one or more needles into a fibroid tumor under direct visual control. Radio frequency current, cryo energy, or microwave energy is then delivered between two adjacent needles (bipolar), or between a single needle and a distant dispersive electrode affixed to the thigh or back of the patient (unipolar). The aim of needle myolysis is to coagulate a significant volume of the tumor, thereby cause substantial shrinkage. The traditional technique utilizes making multiple passes through different areas of the tumor using the coagulating needle to destroy many cylindrical cores of the abnormal tissue. However, the desirability of multiple passes is diminished by the risk of adhesion formation which is thought to escalate with increasing amounts of injured uterine serosa, and by the operative time and skill required. Myolysis can be an alternative to myomectomy, as the fibroids are coagulated and then undergo coagulative necrosis resulting in a dramatic decrease in size. Myolysis is generally limited by its usage with direct visualization techniques, thus being limited to the treatment of subserosal fibroids.

To overcome the limitations of current techniques, it would be desirable to provide a minimally invasive approach to visualize and selectively eradicate fibroid tumors within the uterus. The present invention addresses these and other unmet needs.

BRIEF SUMMARY OF THE INVENTION

The present invention is directed to delivery systems, and methods using the same, having an ultrasound probe for improved imaging and a needle for ablation treatment of target tissues. In an embodiment, the needle is curved with the ultrasound probe having an ultrasound array at a distal portion. In an embodiment, the needle is a curved needle. Typically, the needle will be deployed from within a natural or created body cavity or body lumen. Exemplary body cavities include the uterus, the esophagus, the stomach, the bladder, the colon, and the like. Exemplary body lumens include the ureter, the urethra, fallopian tubes, and the like. Created body cavities include insufflated regions in the abdomen, the thoracic cavity, regions around joints (for arthroscopic procedures), and the like. The present invention will generally not find use with procedures in blood vessels or other regions of the vasculature. Thus, while the following description will be directed particularly at procedures within the uterus for detecting and treating uterine fibroids, the scope of the present invention is not intended to be so limited. In an embodiment, the target tissue is a fibroid within a female's uterus.

In an embodiment, a rigid delivery system comprises a rigid delivery shaft, an imaging core, and an interventional core. In an embodiment, the rigid shaft having a proximal end, a distal end, and an axial passage extending through the rigid shaft. The axial passage will typically extend the entire length of the shaft from the proximal to the distal end, and is open at least at the proximal end. The shaft will usually be rigid along all or a portion of its length, but in other instances may be flexible, deflectable, or steerable.

In an embodiment, the imaging core preferably comprises an ultrasound imaging insert or probe disposed within the axial passage, usually being removably disposed so that it may be removed and replaced to permit sterilization and re-use. The imaging insert will have an ultrasound array within a distal portion thereof. In an embodiment, the ultrasound array is tilted relative to a shaft axis so as to provide an enhanced field of view, as discussed in more detail below. The ultrasound array may be tilted at an angle in a range from about 7 degrees to about 15 degrees, preferably in a range from about 7 degrees to about 10 degrees. It will be appreciated that the interventional core may be adapted for any conventional form of medical imaging, such as optical coherence tomographic imaging, direct optic visualization, and as such is not limited by ultrasonic imaging.

In an embodiment, the ultrasound imaging insert further comprises a flat viewing window disposed over the ultrasound array at the distal portion. The distal end of the rigid shaft may comprise a mechanical alignment feature, as for example, a flat viewing surface for axial or rotational orientation of the ultrasound imaging insert within the shaft. The flat viewing surface will be visually transparent to permit imaging from within the axial passage by the imaging insert. It will be appreciated, however, that the transparent visualization window which aids in physical alignment does not have to be visually transparent for ultrasound. For example, at least a portion of the flat viewing surface may be composed of an ultrasonically translucent material to permit ultrasonic imaging though the surface of the shaft. Further, the re-usable ultrasound imaging insert may be acoustically coupled to the outer delivery shaft to ensure that the ultrasound energy effectively passes from one component to the other. Ultrasonic acoustic coupling may be accomplished in several ways by one or a combination of means, including a compliant material (e.g., pad, sheet, etc.), fluid (e.g., water, oil, etc.), gel, or close mechanical contact between the rigid shaft and ultrasound imaging insert.

In an embodiment, the rigid delivery shaft preferably has a deflectable or fixed pre-shaped or pre-angled distal end. The delivery shaft distal end may be deflected or bent at an angle in a range from about 0 degrees to about 80 degrees relative to the shaft axis, preferably in a range from about 10 degrees to about 25 degrees. The ultrasound imaging insert will usually be flexible (and in some instances deflectable or steerable) so that the distal portion of the ultrasound imaging insert is conformable or bendable to the same angle as the shaft deflectable distal end. The cumulative effect of array tilting and shaft bending advantageously provides an enhanced viewing angle of the ultrasound imaging insert, which is in a range from about 7 degrees (i.e., angle due to tilted ultrasound array) to about 90 degrees relative to the shaft axis.

In a preferred embodiment, the viewing angle is about 20 degrees, wherein the array tilting and shaft bending are at about 10 degrees respectively. It will be appreciated that several geometries of array tilting and shaft bending may be configured so as to provide the desired viewing angle (e.g., distally forward direction, side-viewing or lateral direction), as for example, viewing of the end within the uterus (e.g., cornua and fundus).

In an embodiment, the interventional core preferably comprises a curved needle coupled to the rigid shaft via a needle guide. Significantly, an angle of needle curvature is dependent upon (e.g., inversely proportional to) the ultrasound array tilt and the shaft bend. For example, an increase in an angle of array tilting or shaft bending decreases an angle of needle curvature. This in turn provides several significant advantages such as allowing a treating physician or medical facility to selectively choose an appropriate needle curvature based upon such indications (e.g., variability in needle curvature). Further, a decrease in the angle of needle curvature provides for enhanced pushability, deployability, and/or penetrability characteristics as well as simplified manufacturing processes. The angle of needle curvature may be in a range from about 0 degrees to about 80 degrees relative to an axis, preferably the angle is about 70 degrees when the viewing angle is about 20 degrees. The curved needle generally comprises a two-piece construction comprising an elongate hollow body and a solid distal tip. The solid tip may comprise an asymmetric or offset trocar tip. For example, the tip may comprise a plurality of beveled edges offset at a variety of angles. It will be appreciated that the needle may take on a variety of geometries in accordance with the intended use.

In an embodiment, the needle extends adjacent an exterior surface of the rigid delivery shaft. In an embodiment, the needle is disposed within a needle guide which extends along an exterior of the rigid shaft. The curved needle may be removably and replaceably disposed within the guide passage. The guide passage will typically extend approximately the entire length of the shaft and be open at least at the distal end so as to allow the needle to be reciprocatably deployed and penetrated into adjacent solid tissue. In an embodiment, the needle has a hollow body and a solid distal tip formed from conductive material. The needle, optionally, may be covered, at least along a distal portion of the needle body, with a sheath. In an embodiment, the sheath is retractable such that the needle distal tip is extendable from a sheath's distal end thereby adjusting the length of the exposed conductive distal tip. In an embodiment, the sheath is formed from non-conductive material such as parylene.

In an embodiment, the curved needle and needle guide have a flattened oval shape that has a wideness that is greater than a thickness. This oval cross sectional shape is intended to inhibit lateral deflection during deployment or penetration of the needle. The needle is configured to deliver to the target site radio frequency energy (or other ablative energy such as, but not limited to, electromagnetic energy including microwave, resistive heating, cryogenic) generated at a relatively low power and for relatively a short duration of active treatment time.

In an embodiment, a delivery system includes a shaft, an imaging core, and an interventional core. The delivery shaft has a proximal end, an angled distal tip, and an axial passage therethrough. The imaging core comprises an ultrasound imaging insert disposed within the axial passage. The imaging insert has an ultrasound array within a distal portion thereof, wherein the ultrasound array is tilted relative to a shaft axis. The interventional core comprises a curved ablation needle coupled to the shaft. An angle of needle curvature may be inversely proportional to the ultrasound array tilt and tip angle.

As discussed above, the geometries of the shaft, imaging insert, treatment needle, and needle guide may be varied in accordance with the intended use. The delivery shaft, ultrasound imaging insert, treatment needle, and/or needle guide may be integrally formed or fixed with respect to one another or preferably comprise separate, interchangeable modular components that are coupleable to one another to permit selective sterilization or re-use, and to permit the system to be configured individually for patients having different anatomies and needs. For example, a sterilizable and re-usable ultrasound insert may be removably positioned within a disposable shaft.

The target site undergoing treatment may be any target site which may benefit from the treatment devices and methods according to the present invention. Usually the target site is a uterus within a female's body. The target site in need of treatment generally has an initial (e.g., prior to treatment) approximate diameter which is greater than about two (2) centimeters ("cm"). Usually, the target site's initial diameter ranges from about 1 to about 6 cm. Normally the initial untreated diameter is about 2 cm.

In an embodiment of methods according to the present invention for visualization and ablation of fibroid tissues needing treatment within a patient's body include providing a visualization and ablation system according the device and system embodiments described herein. In an embodiment, the method comprises inserting a rigid shaft having a proximal end, a distal end, and an axial passage therethrough within a uterus. The distal end of the rigid shaft may then be selectively deflected. An ultrasound imaging insert may then be loaded within the axial passage prior to, concurrent with, or subsequent to shaft insertion, wherein a distal portion of the insert conforms to the deflected shaft distal end. Loading may further involve axially or rotationally aligning the ultrasound imaging insert within the rigid shaft. A needle curvature is then selected by the physician or medical facility from a plurality of needles (i.e., at least two or more) having different curvatures based on at least an angle of the deflected shaft distal end. The selected curved needle is then loaded along the rigid shaft. Under the guidance of the imaging system, the needle is inserted into the tissue site. The RF generator is set to deliver and/or maintain a target temperature at the target site for a treatment period.

In an embodiment, the ultrasound array may be tilted or inclined within the distal portion of the insert, wherein selecting the needle curvature further comprises accounting for the ultrasound array tilt. As described above, the ultrasound array is preferably tilted at an angle in a range from about 7 degrees to about 10 degrees relative to a shaft axis. Deflecting will typically comprise pulling a pull or tensioning wire coupled to the shaft distal end in a proximal direction. Deflection occurs at an angle in a range from about 0 degrees to about 80 degrees relative to the shaft axis, wherein the needle curvature is in a range from about 0 degrees to about 90 degrees (i.e., in the case of a non-tilted ultrasound array) relative to an axis. The method further comprises imaging the uterus with a viewing angle of the ultrasound array in a range from about 0 degrees to about 90 degrees (i.e., in the case of a straight needle) relative to the shaft axis, wherein the viewing angle is based upon the deflected shaft distal end and the tilted ultrasound array. It will be appreciated that torquing and/or rotating the rigid device in addition to tip deflection and ultrasound tilt will allow a physician to obtain the desired viewing plane.

In some embodiments, methods further include ablating a uterine fibroid within the uterus with the selected curved needle. In those cases, the needle may be a radiofrequency (RF) electrode, a microwave antenna, a cryogenic probe, or other energy delivery or mediating element intended for ablating or otherwise treating tissue. The distal tip of the needle will usually be adapted so that it will self-penetrate into the tissue as it is advanced from the needle guide. The direction of advancement will be coordinated with the imaging field of the ultrasound insert so that the penetration of the curved needle can be viewed by the physician, usually in real time. Further, an electrolyte (e.g., saline) or other agent may be infused within the uterus prior to or concurrently with fibroid ablation so as to enhance the therapeutic effect provided by the treatment needle. This is preferably accomplished by providing at least one or more (e.g., two, three, four, five, etc.) infusion holes or apertures on the needle body. In still other cases, the needle could be a hollow core needle intended for sampling, biopsy, otherwise performing a diagnostic procedure.

In an embodiment, the power and temperature are generated by a radio frequency energy generator. The radio frequency energy generator is generally configured to deliver energy at a power from about 1 to about 50 watts ("W"), generally from about 1 to about 40 W, usually from about 20 to about 40 W, and normally about 30 W. The radio frequency energy generator is further configured to provide a target temperature at the target site ranging from about 50 to about 110 degrees Celsius ("° C."), usually from about 60 to about 100° C., normally about 90° C. In an embodiment, the needle's conductive tip is at approximately body temperature as it is initially disposed within the patient's body.

In an embodiment, the target site is treated for a period of time ranging from about 1 to about 10 minutes, generally from about 1 to about 8 minutes, usually from about 3 to about 8 minutes, normally about 6 minutes.

In an embodiment, at least one fluid lumen extends along the rigid shaft for delivering fluids to a distal portion of the delivery system. The at least one fluid lumen may be configured for delivery of any one or more of fluids such as those for enhancing acoustic coupling between the ultrasound imaging insert and the target site, contrasting dyes, therapeutic agents, and the like. In an embodiment, the at least one fluid lumen includes acoustic coupling lumens including an internal lumen extending along the axial passage and terminating at an internal port within its distal end and an external lumen extending along the axial passage and terminating at an external port in fluid communication with the outside of the axial lumen. In an embodiment, the external lumen is formed by an external hollow tubular body extending along the needle guide, while the internal lumen is formed by an internal hollow tubular body extending along the underside of the axial hollow tubular body forming the axial passage. It should be appreciated, however, that the external and internal fluid lumens may be oriented in any other suitable location along the shaft. In the embodiment, as shown, the external lumen is located along the needle guide such that the fluid may exit near the ultrasound window, while the internal lumen extends along the underside of the axial hollow tubular body which forms the axial passage so as to allow the fluid to be delivered to the inner tip without trapping air inside the shaft.

In an embodiment, the present invention includes a visualization and ablation system generally having a delivery device, an ultrasound imaging probe detachable from the delivery system, a radio frequency energy generator, and an ultrasound system.

BRIEF DESCRIPTION OF THE DRAWINGS

The following drawings should be read with reference to the detailed description. Like numbers in different drawings refer to like elements. The drawings illustratively depict embodiments including features of the present invention. The drawings are not necessarily drawing to scale and are not intended to limit the scope of the invention.

FIGS. 2A through 2D illustrate exploded views of the distal portion of the ultrasound imaging insert of FIG. 1A in a straight configuration.

FIGS. 7A through 7D illustrate the exemplary features of an ablation needle for use with the visualization and ablation system of FIGS. 4A-4C.

DETAILED DESCRIPTION OF THE INVENTION

Figure 1A:
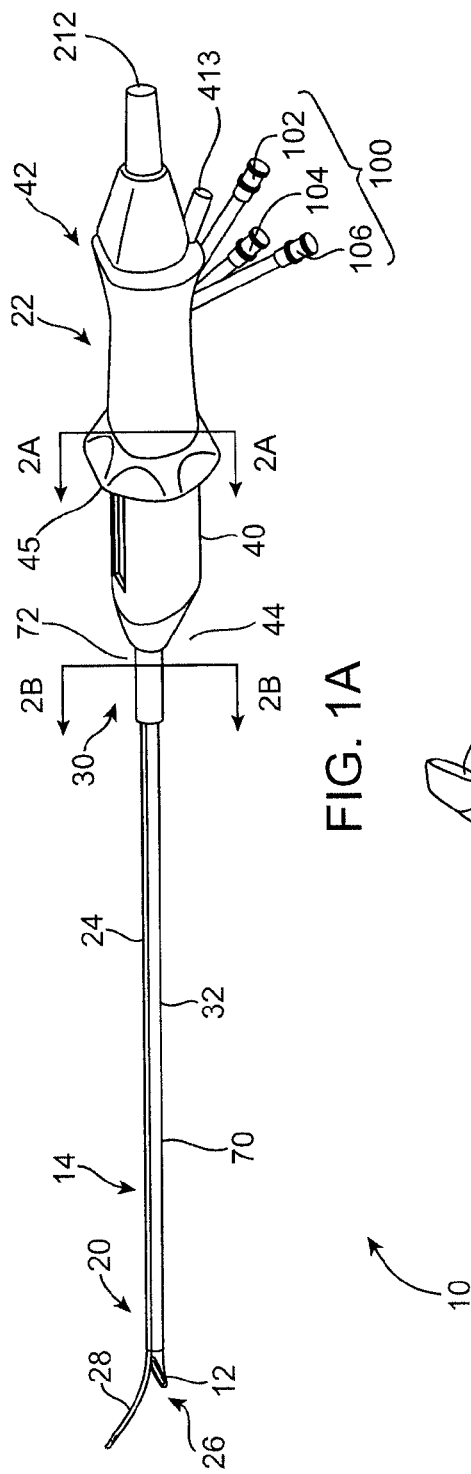
FIGS. 1A through 1E illustrate an exemplary delivery system embodying features of the present invention and having an inclined ultrasound array for improved imaging and a curved needle for ablation treatment.
Figure 1B:
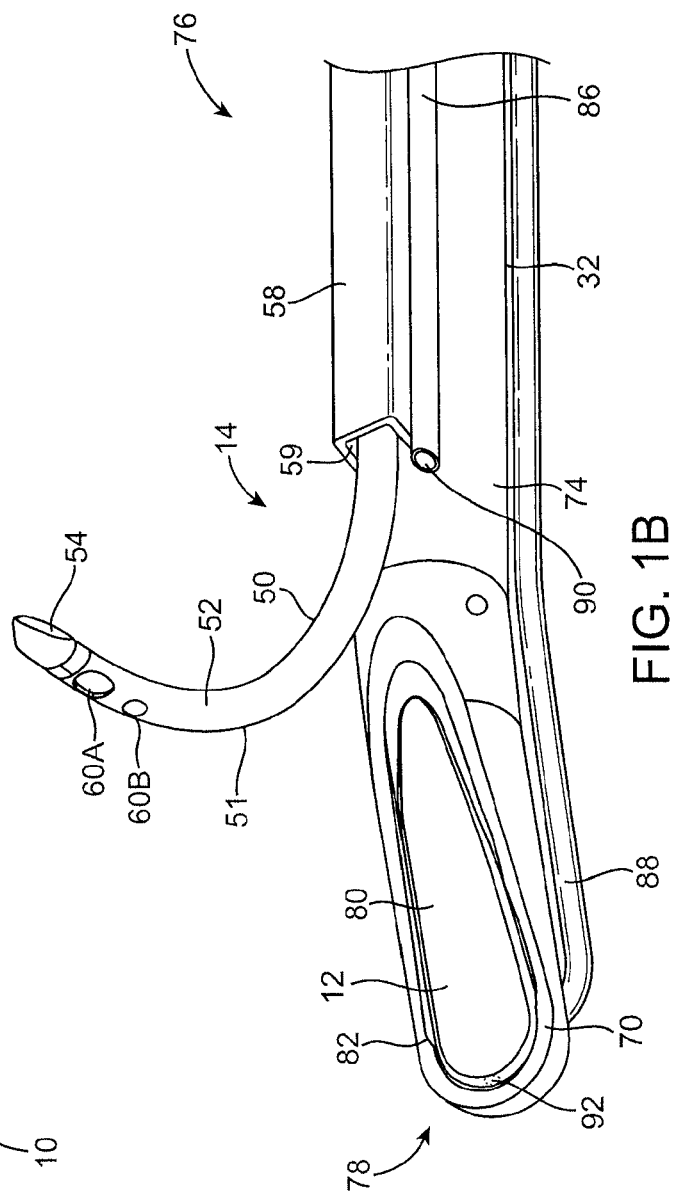
Figure 1C:
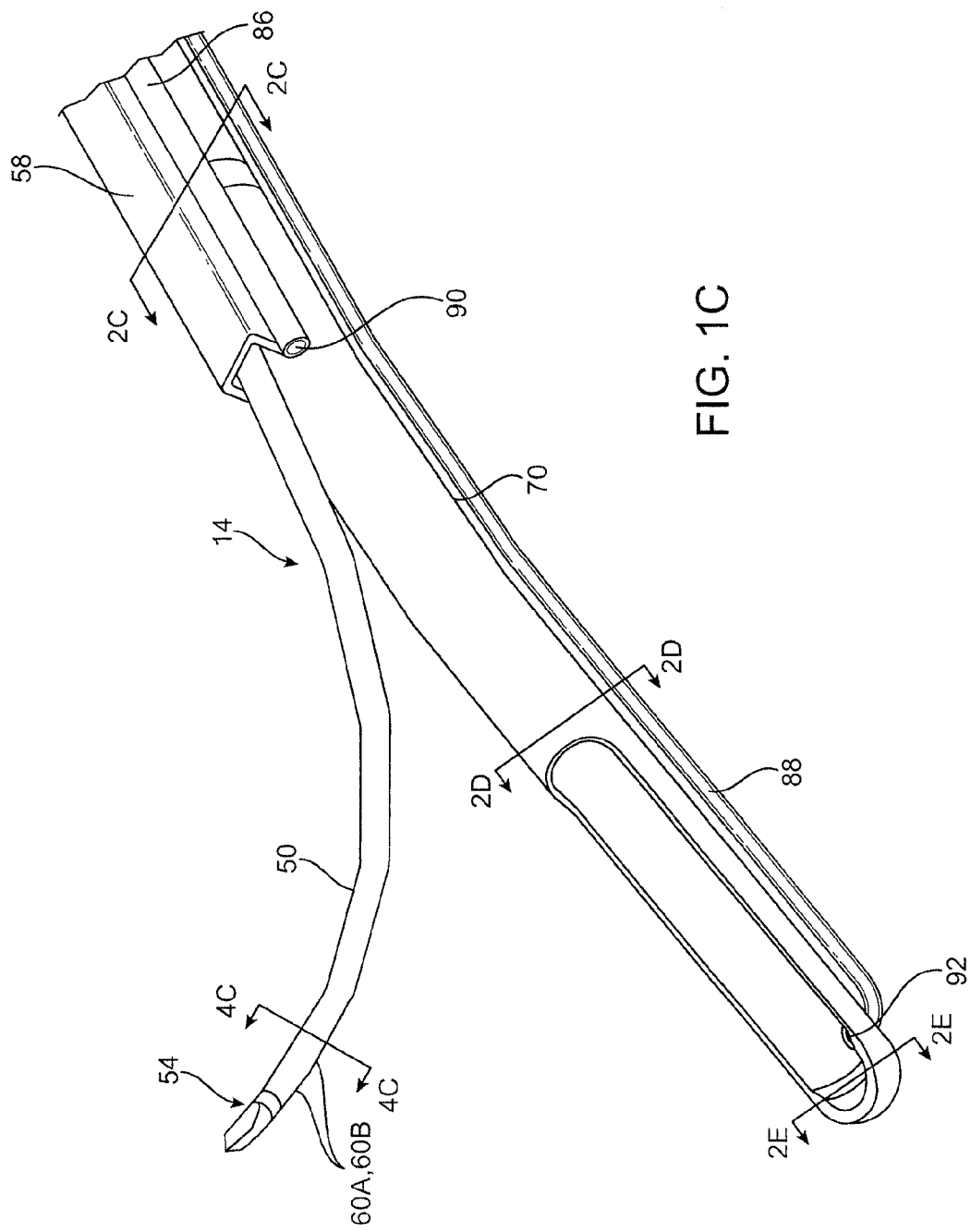

Referring to FIGS. 1A through 1C, an exemplary delivery system 10 embodying features of the present invention is shown having a shaft inclined viewing window 12 for improved imaging and a curved needle 14 for ablation treatment of a target site 16 such as fibroid tissues 18 (FIG. 3E) within a female's reproductive system. The delivery system 10 includes a system distal end 20, a system proximal end 22, and a rigid delivery shaft 24. Delivery shaft 24 includes a shaft distal end 26 with a bent or deflectable shaft distal tip 28, a shaft proximal end 30, and an axial passage 32 extending longitudinally through at least a portion of the delivery shaft 24. A handle 40 with handle proximal and distal ends 42 and 44, is attachable to the shaft proximal end 30. The handle 40 further includes a longitudinally movable slider 45 for enabling the advancement and retraction of the needle 14 to and from within a needle guide 58.

Figure 3A:
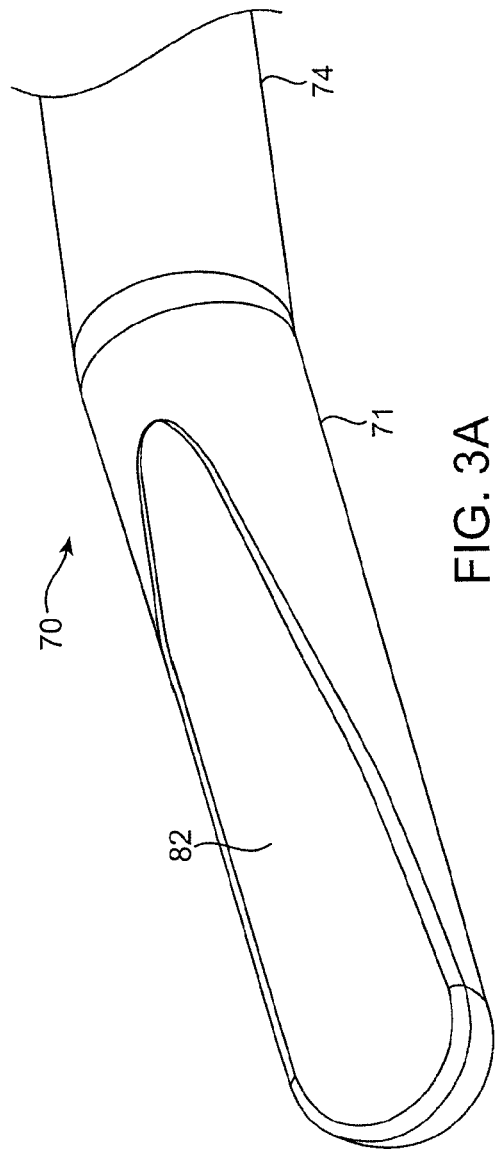
FIGS. 3A through 3D illustrate exploded views of the distal portion of the ultrasound imaging insert of FIG. 1A in a bent configuration.

The curved needle 14 has a needle body 50 with a shaped needle distal end 52 and a solid needle distal tip 54, as best seen in FIGS. 1B-1E and 4A-E. Needle 14 is configured to deliver, to the target site 16 including fibroid 18 (as shown in FIG. 3E), radio frequency energy generated at a relatively low power and for relatively a short duration of time from an ablative energy generator 400 (such as, but not limited to, electromagnetic energy including microwave, resistive heating, cryogenic) including a radio frequency (RF) energy generator 410, as shown in and discussed in reference to FIGS. 3A and 3E. In an embodiment, as shown, needle body 50 is a hollow body forming a needle lumen 51.

Figure 4A:
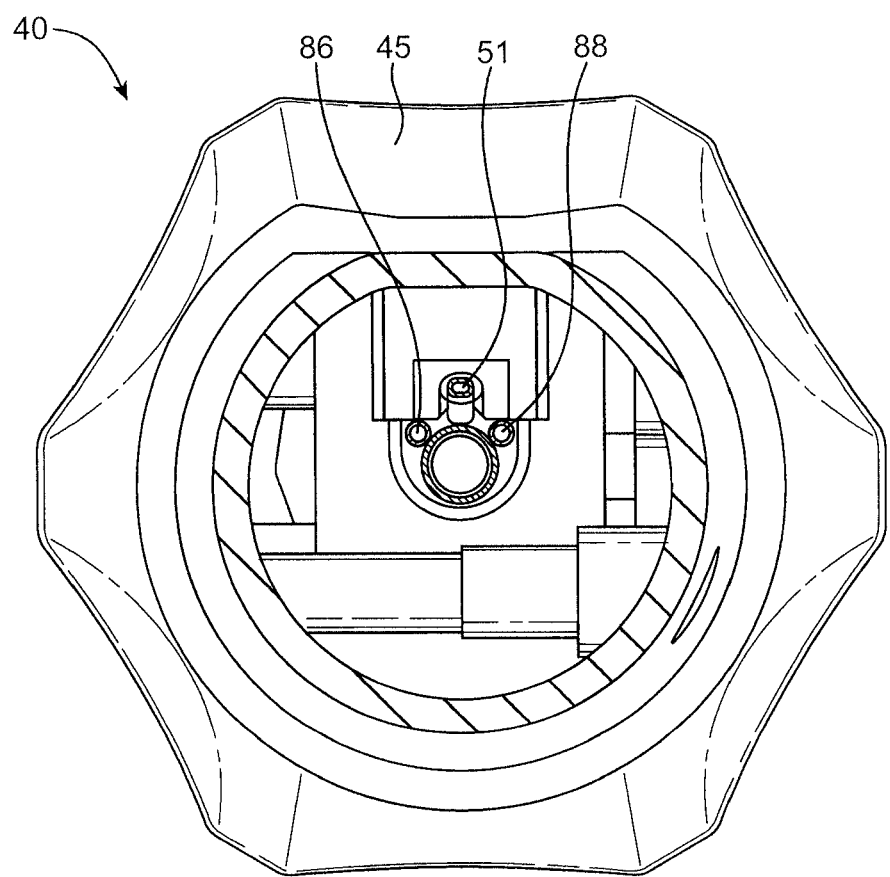
FIGS. 4A through 4E illustrate cross-sectional views of the embodiments of exemplary delivery system of FIGS. 1A through 1C taken along their respective lines.
Figure 4B:
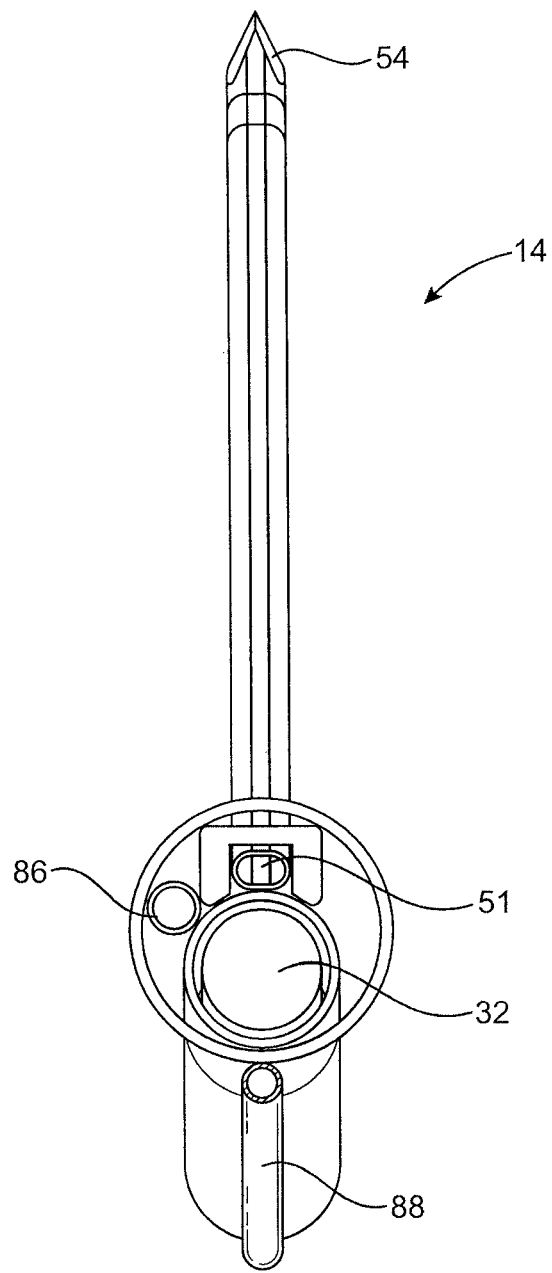
Figure 4C:
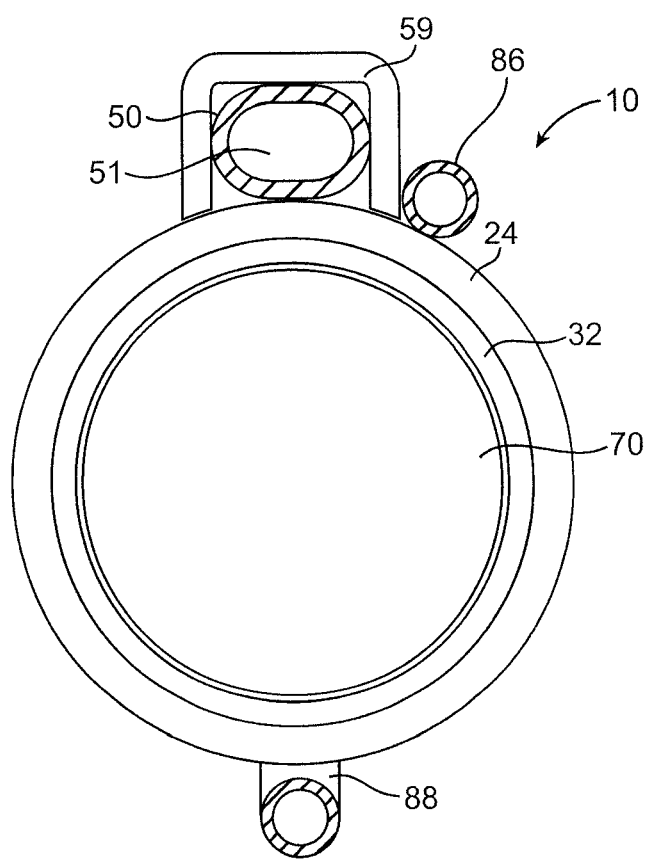
Figure 4D:
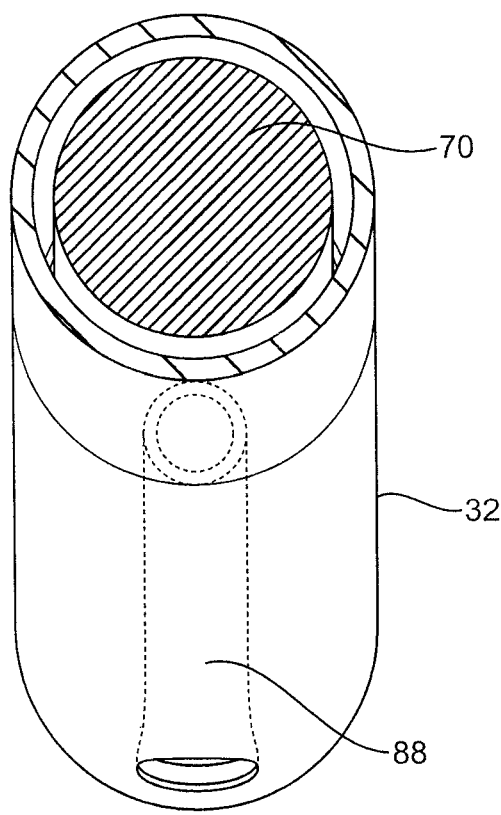
Figure 4E:
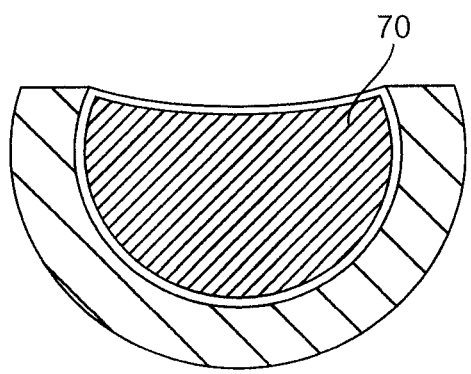

Now referring back to FIGS. 1A and 1B, needle 14 is disposed adjacent the exterior of the shaft 24 within the needle guide 58. Needle guide 58 includes a guide passage 59 and is attachable to the shaft by way of adhesive, or other means such as laser welding, shrink tubing, and the like. Needle 14, as best seen in FIGS. 1B, 4B, and 5C, may include one or more needle apertures 60. As shown, the needle 14 includes two needle apertures 60A and 60B. The most distal aperture 60A exposes the distal end of a thermocouple pair 59a and 59b as shown in FIG. 6C. The proximal aperture 60B may be used for delivery of various therapeutic and/or imaging enhancement fluids and contrasting agents/dyes to the target site 16 and fibroid 18. In the embodiment shown, contrasting dye runs within the lumen 51 of the hollow needle body. As can be seen from FIGS. 2A and 4C, the thermocouple pair 59a and 59b are disposed within the lumen 51 for monitoring the temperature at the target site 16, while the annular space around the thermocouples within lumen 51 is usable for delivery of dyes.

The shaft axial passage 32 is configured for removably and replaceably receiving and housing an ultrasound imaging insert 70. A sealing element 72 may be provided between the ultrasound imaging insert 70 and the shaft handle 40 to provide sufficient sealing around the imaging insert 70 at a proximal end.

Figure 1D:
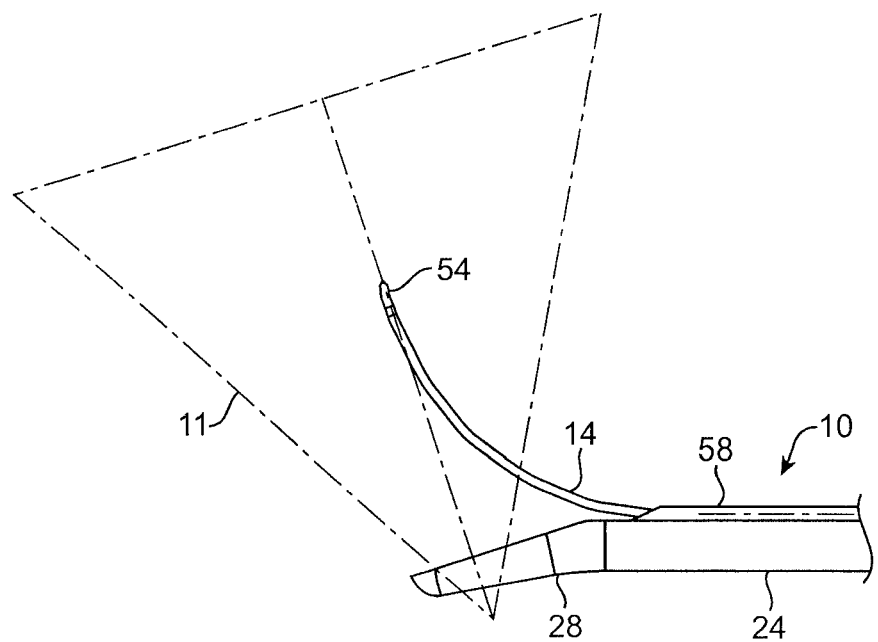
Figure 1E:
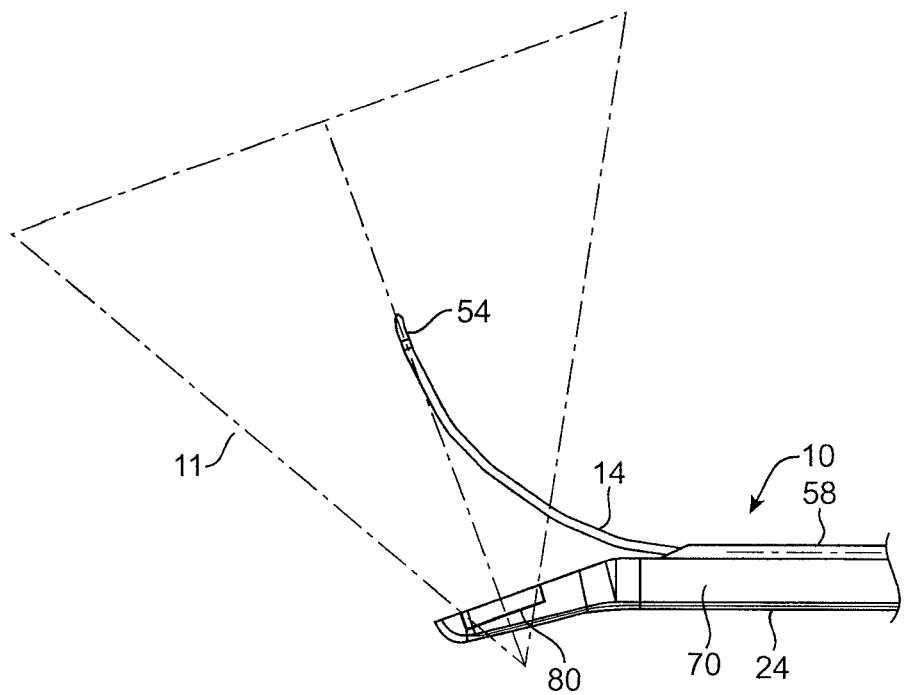

The ultrasound imaging insert 70 as shown in FIG. 1B, and as further described below, comprises an insert flexible shaft 74, an insert proximal end 76, an insert distal end 78, an ultrasound array 80, and an insert flat viewing window 82 disposed at the insert distal end 78. The ultrasound array 80 is viewable from the shaft inclined viewing window 12. The shaft viewing window may be used for axial and/or rotational orientation of the ultrasound imaging insert 70 within the delivery system shaft 24. A simplified illustration of the delivery shaft 24 as shown in FIG. 1D carries the ultrasound imaging insert 70 within its axial passage 32. A viewing plane 11 provided by the tilted and bent ultrasound array 80 is further illustrated.

Referring now to FIGS. 2A through 2D, exploded views of a distal portion 71 of the ultrasound imaging insert 70 are illustrated. FIGS. 2A and 2C show isometric and side views respectively of the ultrasound imaging insert 70 in a straight position prior to insertion into the axial passage 32 of the delivery shaft 24, as will be described in more detail below. The ultrasound imaging insert 70 comprises a flexible shaft 74 and includes an ultrasound array 80 and a flat viewing window 82 within the distal portion 71. FIGS. 2B and 2D illustrate transparent isometric and side views respectively of the ultrasound imaging insert 70, wherein the ultrasound array 80 is shown tilted relative to a shaft axis 39. Preferably, the ultrasound array 80 is tilted or inclined at an angle α in a range from about 7 degrees to about 15 degrees. It will be appreciated that the angle α of inclination of the ultrasound array 80 may comprise a variety of angles (e.g., 0 degrees to about 45 degrees) as permitted by an outer diameter of the flexible shaft 74. The ultrasonic array 80 may be arranged in a phased array, for example either a linear phased array or a circumferential phased array. Alternatively, the ultrasonic imaging array 80 may comprise one or more independent elements, such as parabolic or other shaped imaging elements. In still further embodiments, the ultrasonic imaging array 80 may be arranged in a rotating mechanism to permit rotational scanning.

Figure 3B:
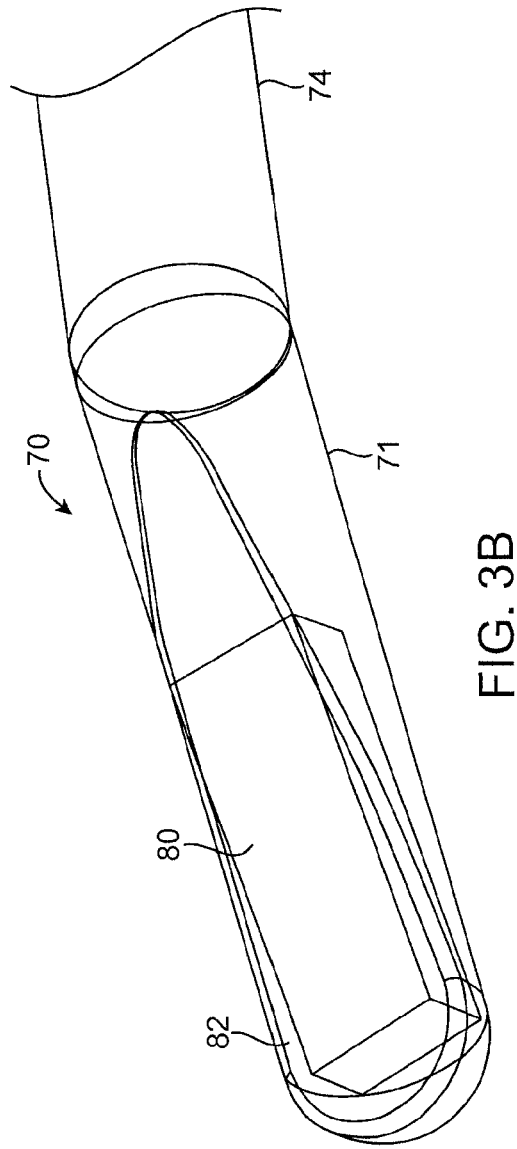
Figure 3C:
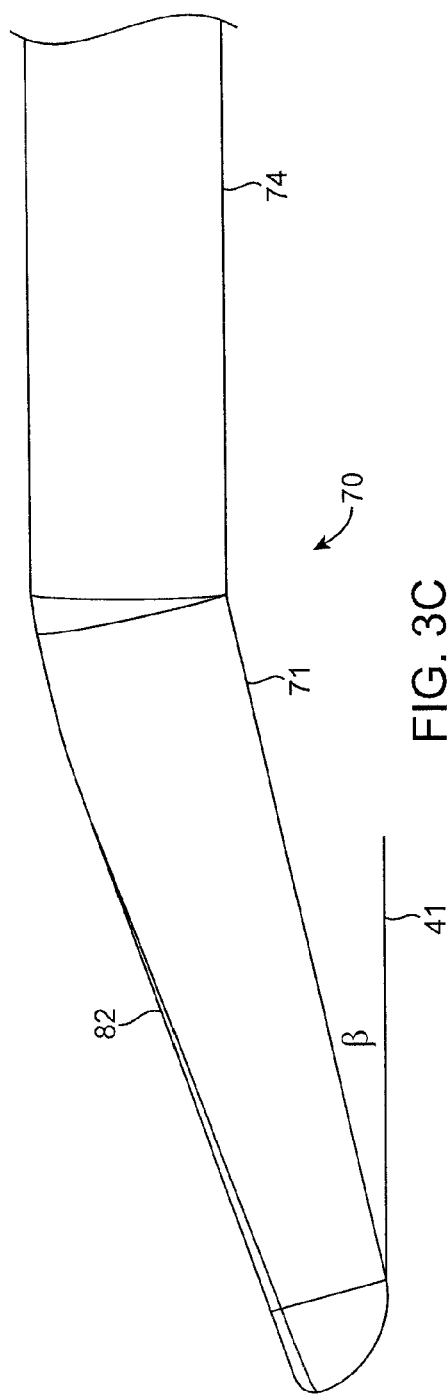
Figure 3D:
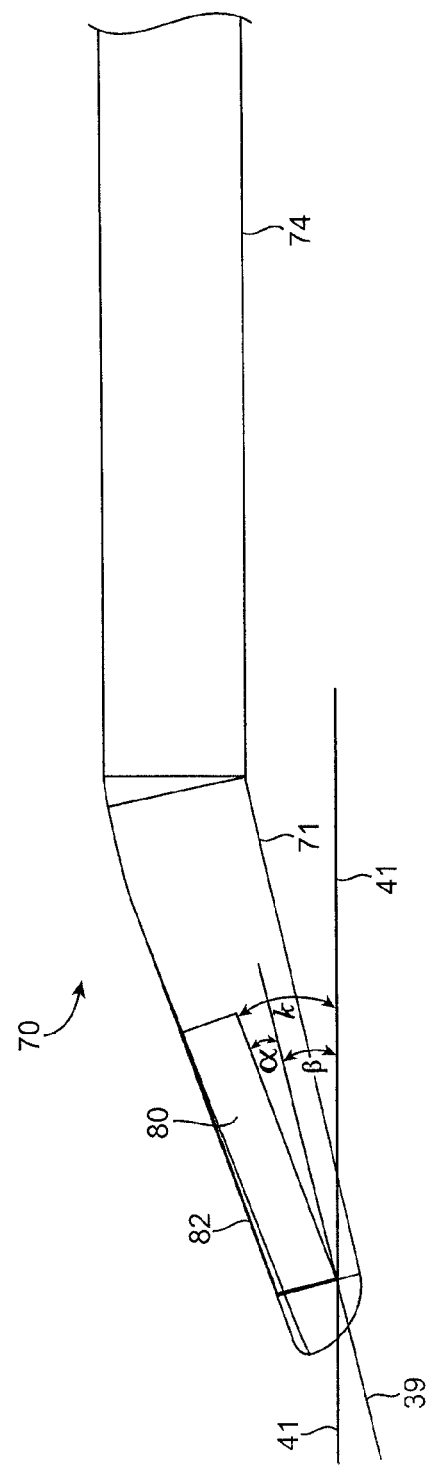

Referring now to FIGS. 3A through 3D, exploded views of a distal portion 71 of the ultrasound imaging insert 70 are further illustrated. FIGS. 3A and 3C show isometric and side views respectively of the ultrasound imaging insert 70 in a bent position subsequent to insertion into the axial passage 32 of the delivery shaft 24. In particular, the transparent isometric and side views of FIGS. 3B and 3D illustrate the cumulative effect of tilting the ultrasound array 80 relative to the shaft axis 39 at the angle α and bending the distal portion 71 of the ultrasound imaging insert 70. The bend angle β may be in a range from about 0 degrees to about 80 degrees relative to the shaft axis 41, preferably in a range from about 10 degrees to about 13 degrees. The bend angle β will be determined by the deflectable distal tip 28 of the delivery shaft 24 as the flexible insert 70 conforms to the deflectable distal tip 28 upon insertion within the shaft 24. The viewing angle κ of the ultrasound imaging insert 70 achieved by this cumulative effect may be in a range from about 7 degrees (i.e., angle due solely to tilted ultrasound array 12) to about 90 degrees relative to the shaft axis 40. In the illustrated embodiment, the viewing angle is about 20 degrees, wherein the array tilting is approximately 7 degrees and shaft bending is about 13 degrees.

In an embodiment, the deflectable distal tip 28 of the rigid shaft 24 may be deflected by the use of pull or tensioning wire(s) housed within the shaft 24. Deflection may occur at a true mechanical pivot or at a flexible zone at the shaft distal end 26. When the delivery shaft 24 is deflectable by a user, various needles 14 may be used to match the amount of deflection provided by the distal tip 28 as well as the amount of tilt provided by the ultrasound array 80. Hence, the needle guide 58 will typically be empty until the distal end 26 of the shaft 24 is deflected. For example, the shaft 24 may be inserted in a straight configuration. The distal tip 28 may then be deflected until a target anatomy is identified. A needle 14 is then back loaded within the guide passage 58 that corresponds to the amount of the deflection.

The delivery system 10, as shown in various FIGS. 1 and 2, at the device proximal end 22, includes a plurality of fluid inlet ports 100 in fluidic communication with various portions of the delivery system shaft 24, needle 14, and/or imaging insert 70. In an embodiment, features of which are shown in FIGS. 1A and 2A, system 10, includes fluid inlet ports 102, 104, and 106. Fluid inlet ports 100 (including 102, 104, and 106) are configured to direct various fluids to a distal portion 23 of the delivery system 10. By way of example, fluid inlet port 102 is configured to deliver dyes to at least one of the needle apertures 60, such as aperture 60B at the needle distal end 52; while fluid inlet ports 104 and 106 are configured, respectively, to deliver acoustic coupling fluids through external and internal axial lumens 86 and 88 disposed along axial passage 32 to a shaft external fluid outlet port 90 and a shaft internal fluid outlet port 92 at the shaft distal end 26. Same or different fluid ports, such as fluid port 102, may be further utilized to deliver other fluids such as therapeutic agents to any of the other outlet ports or apertures. Optionally, additional apertures may be provided at desired locations along lumen 51 of the hollow needle body 50.

The shaft 24 of the present invention, as described herein, may serve several functions including delivering ultrasound, diagnostic, and/or interventional treatments, bending of the ultrasound insert via the deflectable distal tip, and/or providing a sterile barrier between the ultrasound and/or interventional components. As shown in FIG. 1B, the delivery shaft 24 carries the ultrasound imaging insert 70 within its axial passage 32.

Generally, the delivery system shaft 24 will have a length in a range from about 20 cm to about 40 cm and an outer diameter in a range from about 3 mm to about 10 mm, while the ultrasound imaging insert 70 will have a length in a range from about 50 cm to about 90 cm and an outer diameter in a range from about 2 mm to about 4 mm. Delivery system shaft 24 and the ultrasound imaging insert 70 may be acoustically coupled in one or more of several ways to enable the effective passage of ultrasound energy from one component to the other. For example, the ultrasound insert 70 may be placed in close mechanical contact with the shaft 24 so as to provide a dry coupling. In addition or alternatively, a thin compliant layer (e.g., pad or sheet) may be disposed between the viewing windows 82 and 12, of the ultrasound insert 70 and the shaft 24, respectively, so as to provide further interference between such components. It will be appreciated that a thinner layer may be preferred to minimize unwanted acoustic loss, index of refraction, impedance, and/or other material property effects. Alternatively, or in addition to, the shaft axial passage 32 in which the ultrasound imaging insert 70 is disposable, may be filled with a fluid (e.g., water or oil) or gel to further provide a wet coupling between the shaft and the imaging insert which may compensate for any mechanical tolerances.

Figure 5A:
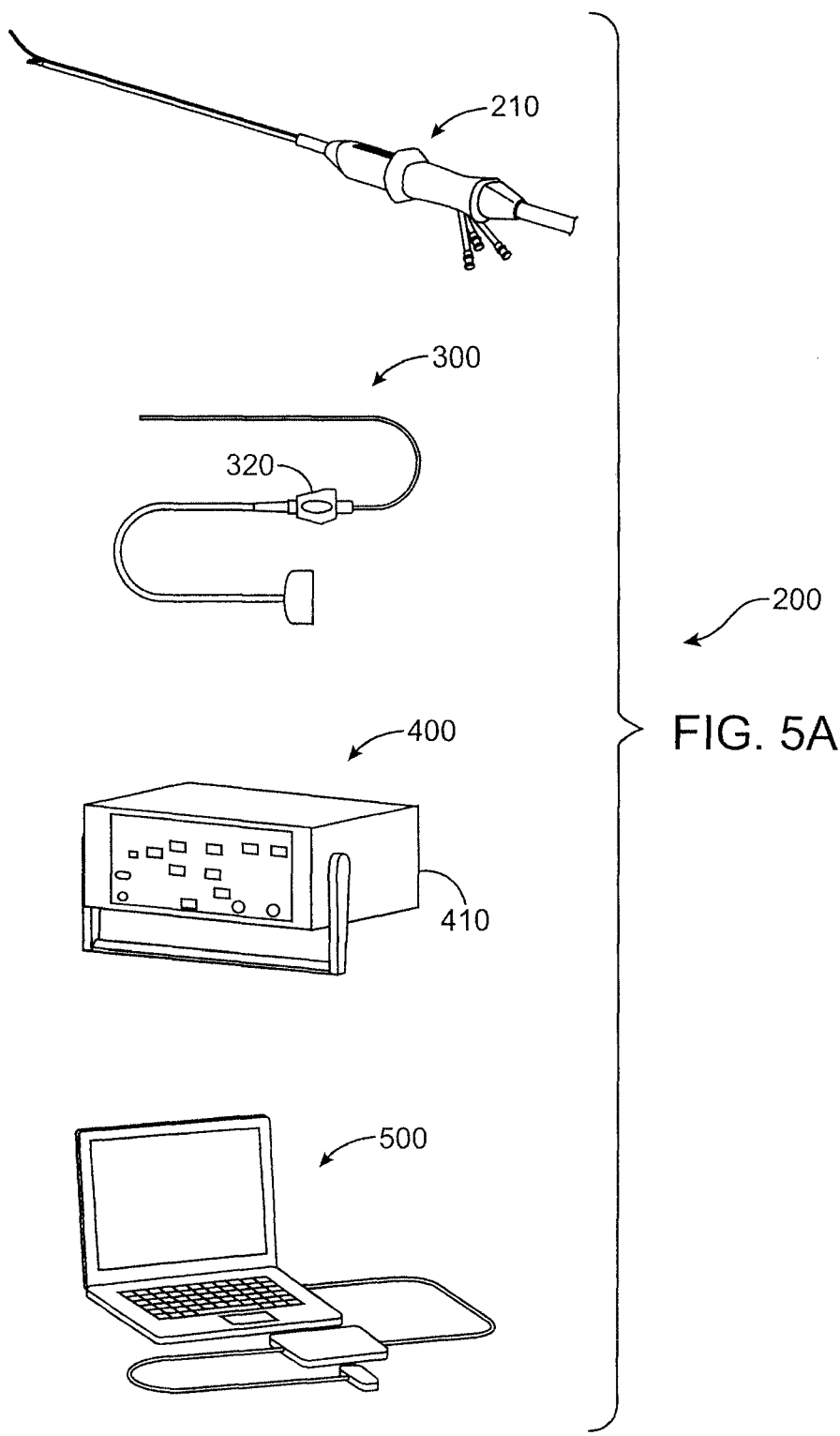
FIG. 5A illustrates a visualization and ablation system embodying features of the present invention.

Now referring to FIG. 5A, a visualization and ablation system 200 embodying features of the present invention is shown, including a delivery device 210, an ultrasound imaging probe 300 being detached from the delivery system 210, the radio frequency energy generator 410, and an ultrasound system 500. The various components of the exemplary visualization and ablation system 200 will be further described in individual detail.

Figure 5B:
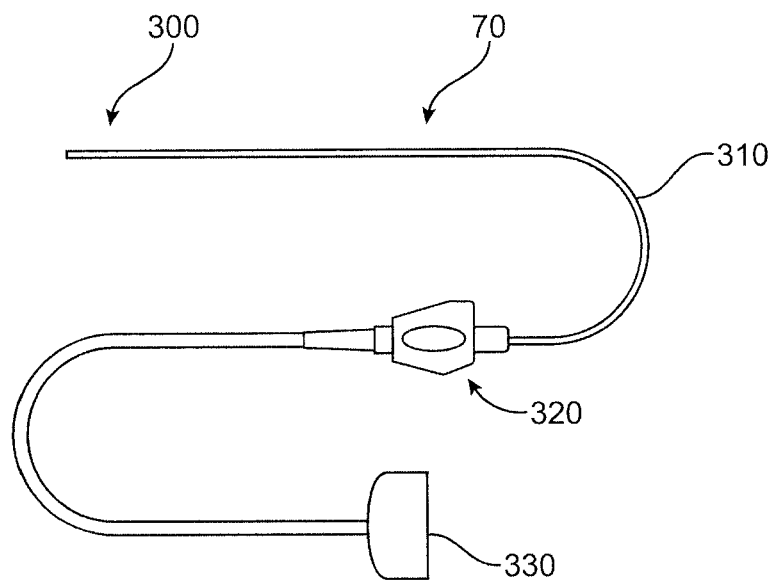
FIG. 5B illustrates features of an exemplary ultrasound probe of the visualization and ablation system of FIG. 5A.
Figure 5C:
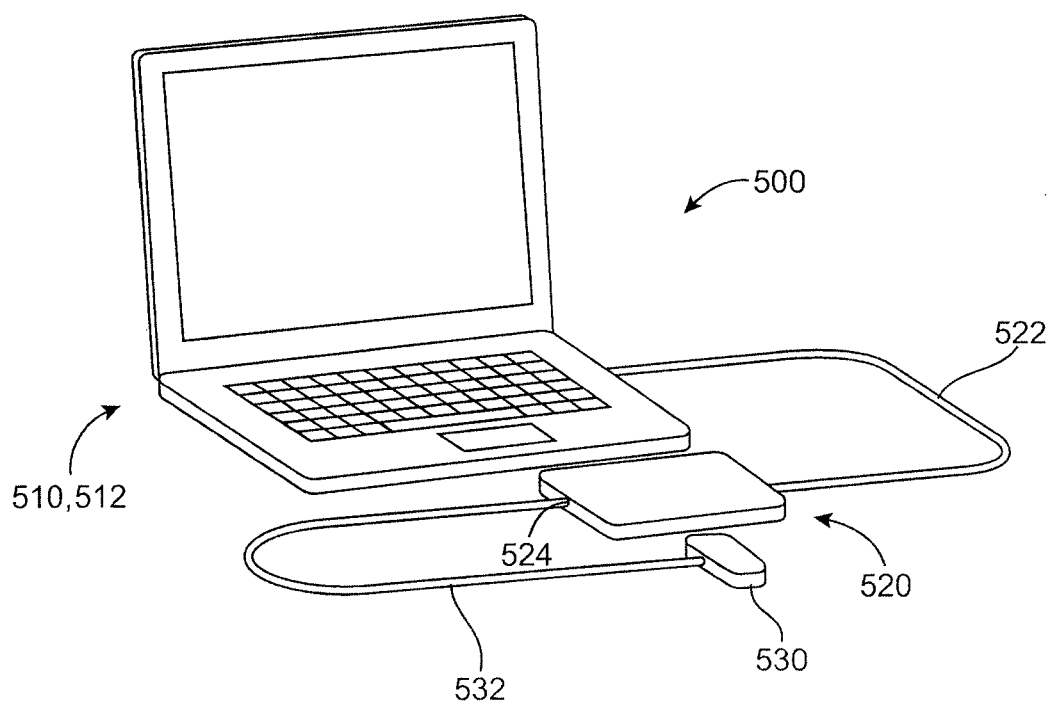
FIG. 5C illustrates features of an exemplary ultrasound system of the visualization and ablation system of FIG. 5A.

The ultrasound probe 300 embodying features of the present invention, as shown in FIG. 5B, generally includes the imaging insert 70 as generally described above, and is connectable to an imaging insert probe port 212 at the delivery system proximal end 22. The ultrasound probe 300 includes an alignment element 320 for removably engaging with the system probe port 212 of the delivery system 210 through a probe cable 310. Alignment element 320 is connectable to the ultrasound system 500 by way of an ultrasound probe attachment element 330.

The ultrasound system 500, embodying features of the present invention, as shown in FIG. 5C, generally includes a CPU 510 such as one shown operable by a laptop computer 512. The CPU 510 is connectable to a beam former 520 by way of a communications cable (such as a firewire cable) such as an ultrasound cable 522. The beam former 520 at a beam former distal end 524 is connectable to a probe attachment element 530 by a probe extension cable 532.

Figure 5D:
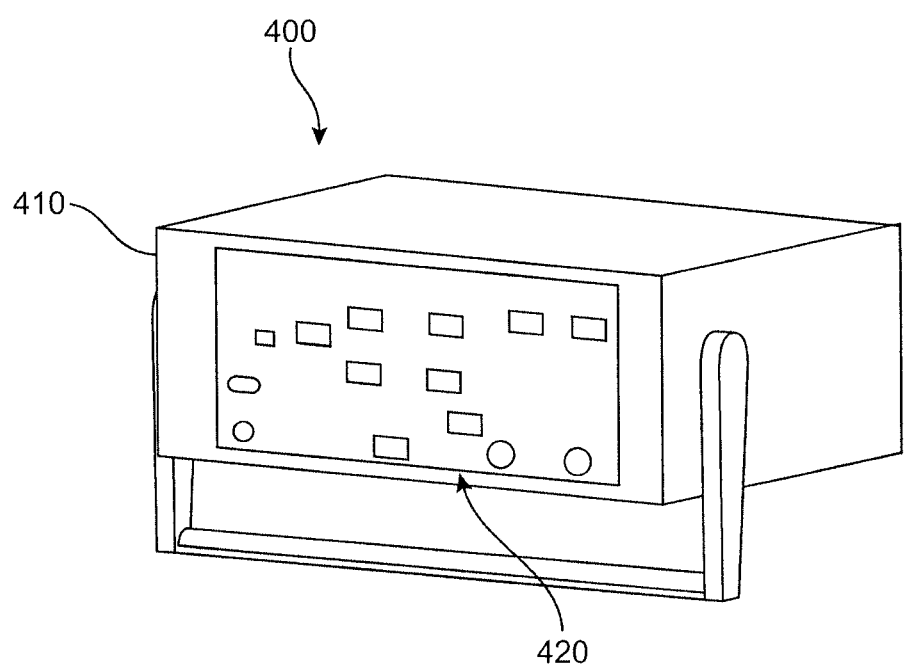
FIG. 5D illustrates features of an exemplary radio frequency energy generator of the visualization and ablation system of FIG. 5A.
Figure 5E:
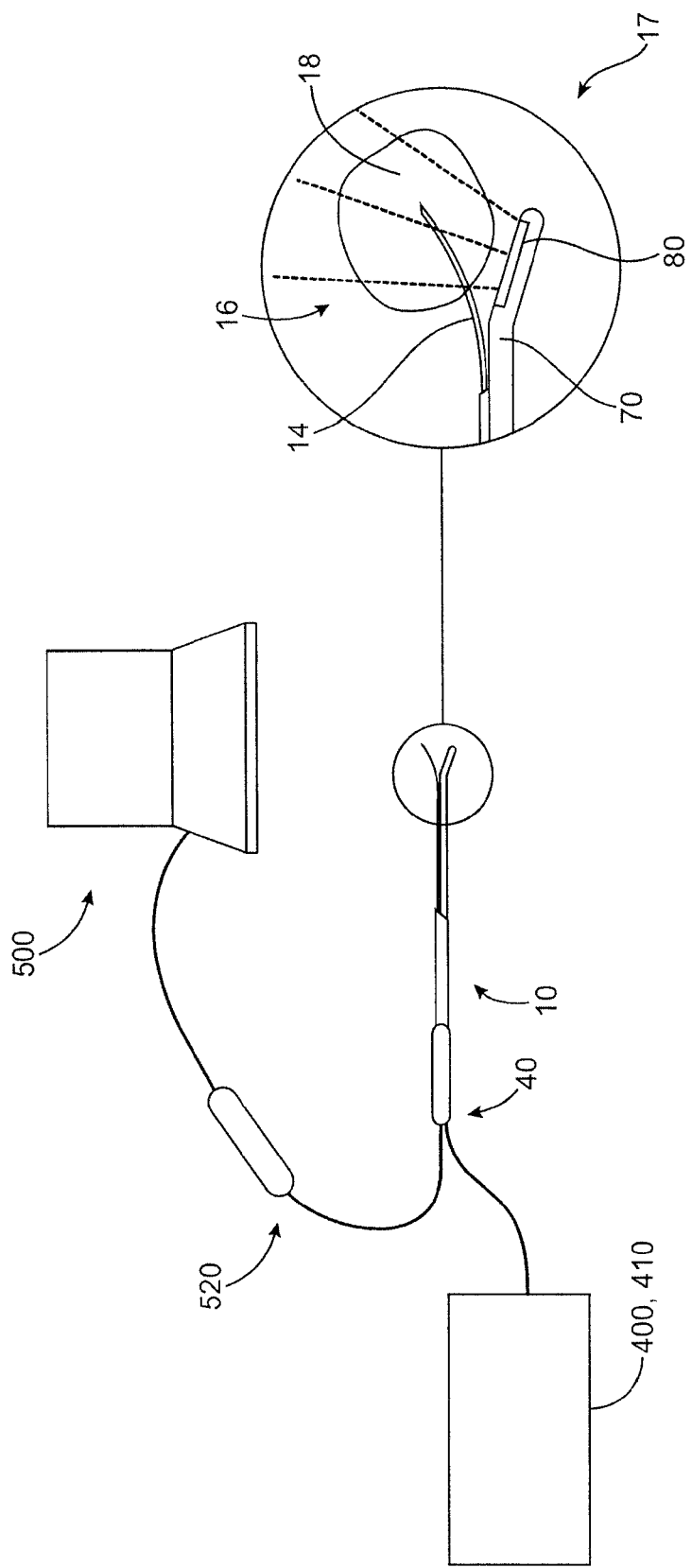
FIG. 5E illustrates the visualization and ablation system of FIG. 5A as disposed during operation within a uterus for the treatment of fibroids in accordance with the features of the present invention.

The radio frequency energy 410, embodying features of the present invention, and as shown in FIGS. 5D and 5E, is generally connectable to the delivery system 210 including needle 14, through energy outlet port 420. A suitable cable (not shown) removably connects energy outlet port 420 to a needle port 413 at the proximal end 22 of the handle 40. Radiofrequency energy is delivered from the radio frequency generator 410 to fibroid 18 at the target site 16 through needle 14 which is disposed within the needle guide 58.

Figure 6A:
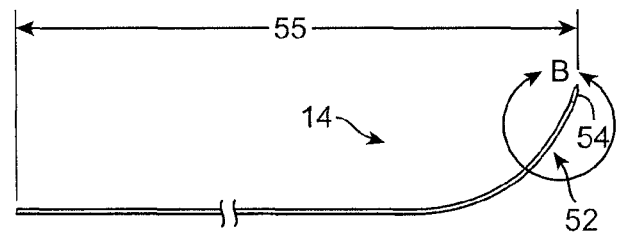
FIGS. 6A through 6C illustrate the exemplary features of an ablation needle for use with the visualization and ablation system of FIG. 5A.
Figure 6B:
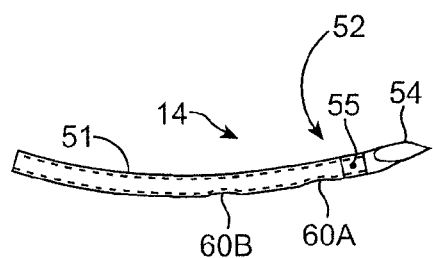
Figure 6C:
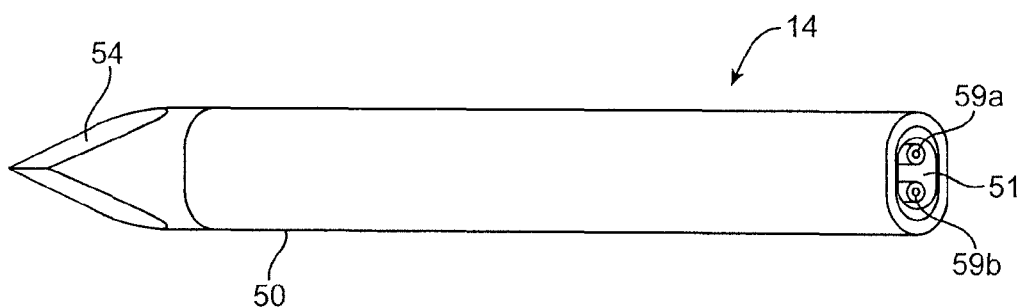

Now referring to FIGS. 6A-6C, needle 14 embodying features of the present invention, is shown disposed within the needle guide 58 which extends along the exterior of shaft 24. As further shown in cross-sectional FIGS. 7B-7D, the curved needle 14 generally comprises a two-piece construction including the elongate needle hollow body 50 with the shaped needle distal end 52 and the solid needle distal tip 54. The needle distal tip 54 may be laser welded 55 to the needle hollow body 50 as shown in FIG. 6B. The needle distal tip 54 may also be attached via alternative means, for example, adhesives or mechanical features or fits. Generally the needle hollow body 50 will have a length 55 in a range from about 20 cm to about 45 cm, an oval cross section having a thickness 57 in a range from about 0.5 mm to about 2 mm, and a wideness 59 in a range from about 1 mm to about 3 mm. In an embodiment, as shown in FIG. 7B, the oval cross section is flattened minimizing lateral deflection during deployment and penetration of the needle 14. In an embodiment, as shown in FIGS. 6B and 6C, there are two laser cut infusion apertures 60 within the tubular body 50 for the infusion of agents (e.g., electrolytes, drugs, etc., dyes/contrasts) so as to enhance either or both the visualization and therapeutic effect of the needle 14 prior to, during, or after the ablation treatment. The infusion apertures 60 may be aligned on one side of the tubular body 50. Generally, the infusion apertures have a length 63 in a range from about 0.5 mm to about 2 mm and a width 65 in a range from about 0.5 mm to about 2 mm.

As best seen in FIG. 7A, the hollow tubular body 58 may be curved at an angle θ in a range from about 0 degrees to about 80 degrees relative to an axis 65 so as to access side/lateral fibroids. In this depiction, the angle θ is about 70 degrees. Significantly, the angle of needle curvature θ is dependent upon the ultrasound array tilt angle α and the shaft bend angle β. For example, an increase in the tilt angle α or bend angle β decreases the angle of needle curvature θ. This in turn advantageously allows a treating physician to selectively choose an appropriate needle curvature from a plurality of needles 14 (i.e., at least two or more) having different curvature angles θ.

Figure 9A:
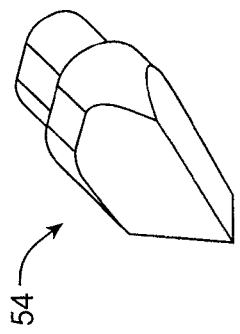
FIGS. 9A through 9E further illustrate the asymmetric solid distal tip of FIG. 6A.
Figure 9B:
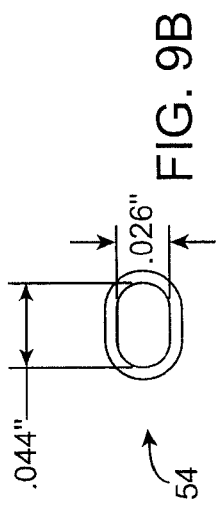
Figure 9C:
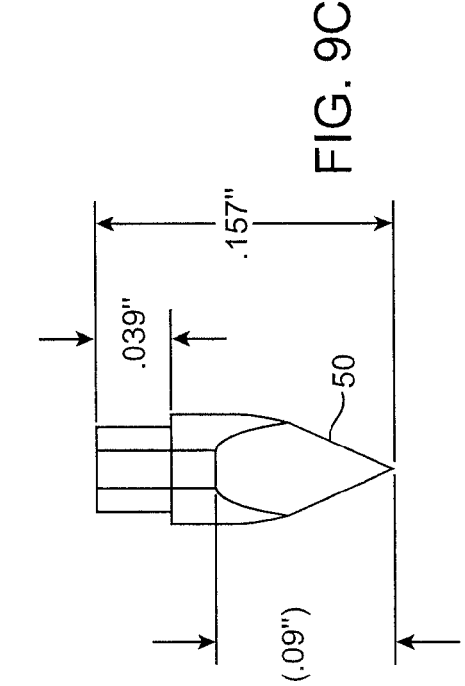
Figure 9D:
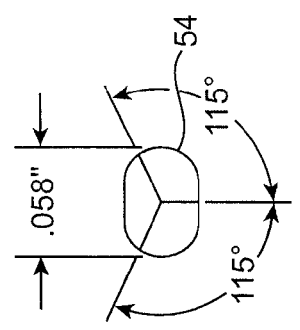
Figure 9E:
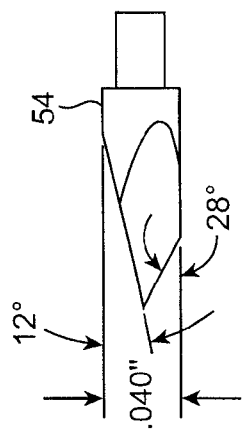

Referring now to FIGS. 9A through 9E, in an embodiment, the solid tip 54 may comprise an asymmetric or offset trocar tip. The center point of the tip 54 may be offset from a centerline of the needle to help compensate for any needle deflections due to tenacious tissue, in effect steering the needle towards the intended target even with the deflection. For example, the tip 54 may comprise a plurality of beveled edges offset at a variety of angles as illustrated in FIGS. 9D and 9E.

The needle body 50 is formed from an RF energy conductive material such as stainless steel. As will be appreciated, the solid tip 54 may comprise a variety of dimensions and shapes and is not limited to FIGS. 9A-9E. It will be further appreciated that the tip 54 need not be a separate component but may alternatively be integrally formed with the needle body 50. The needle 14, including the tip 54 and tubular body 50 may be formed from a variety of materials including stainless steel, nitinol, and the like, for transmitting ablation energy. As best seen in FIG. 1A, the handle 40 may have a needle advancement portion to reciprocatably advance or retract the needle 14 from within the needle guide 58. The needle advancement portion, as shown, is in partially advanced position for complete deployment of the needle 14. The needle guide 58 will further have an oval cross section similar to that of the needle 14, with a thickness in a range from about 0.5 mm to about 2 mm and a wideness in a range from about 1 mm to about 3 mm. The flattened guide 58 and flattened needle 14 as shown in FIG. 4C are intended to minimize lateral deflection during deployment or penetration of the needle 14 into the tissue.

Figure 8A:
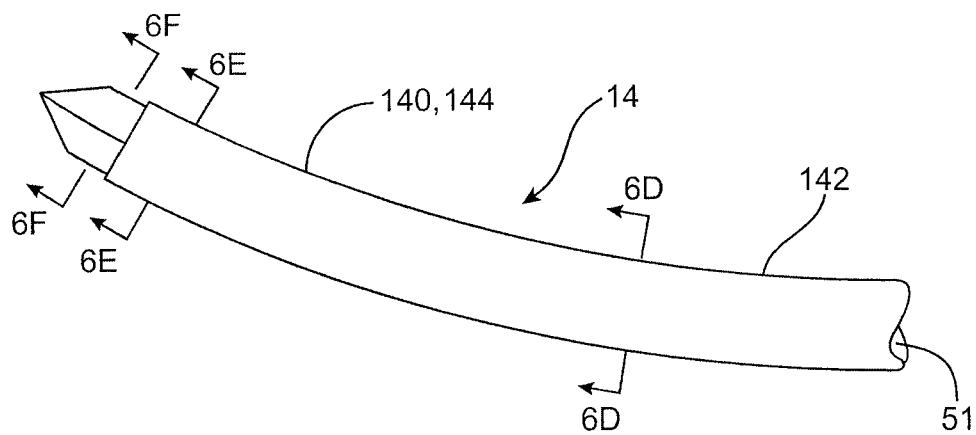
FIG. 8A illustrates an exemplary ablation needle for use with the visualization and ablation system of FIG. 5A and including an insulating material such as a retractable sheath.
Figure 8B:
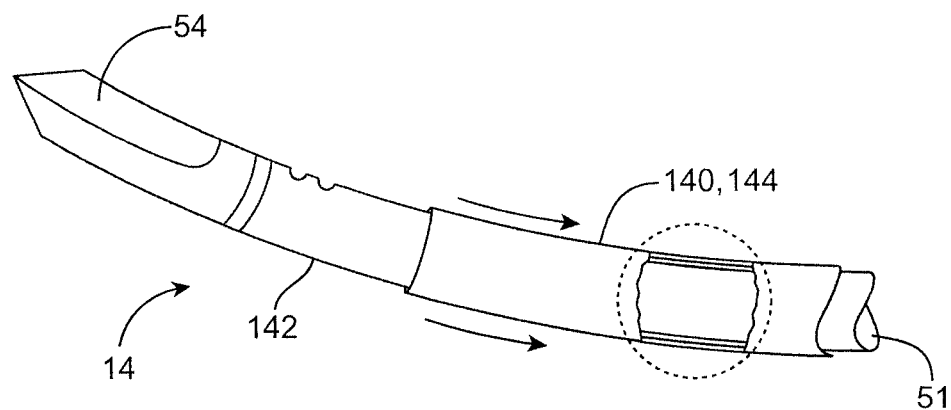
FIGS. 8B through 8C illustrate the needle of FIG. 8A with the retractable sheath in a retracted position.
Figure 8C:
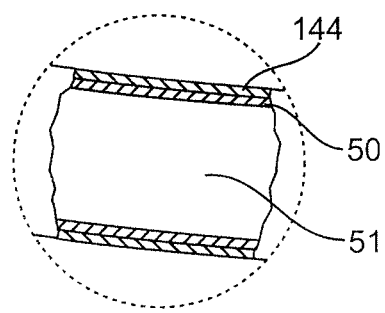
Figure 8D:
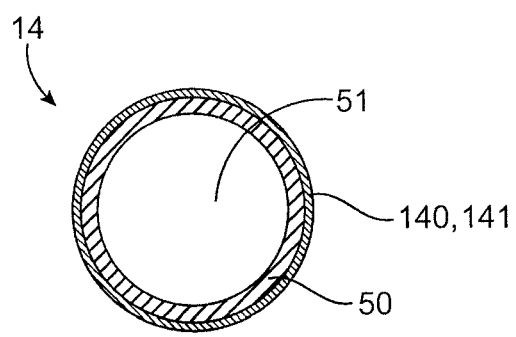
FIGS. 8D through 8F are cross-sectional views of the needle of FIG. 8A taken along lines 8D-8D, 8E-8E, and 8F-8F.
Figure 8E:
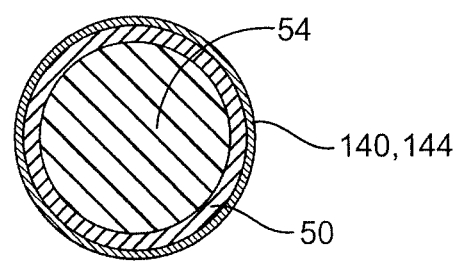
Figure 8F:
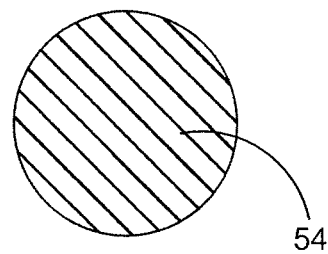

In an embodiment, as shown in FIGS. 8A-8C, an insulating material 140 extends longitudinally along at least an exterior portion 142 of the needle 14 terminating proximal to the conductive needle distal tip 54. In an embodiment, features of which are shown in FIGS. 8D-8E, the insulating material 140 forms a retractable sheath 144. The conductive needle distal tip 54 is extendable from a distal end 146 of the retractable sheath 144. The proximal retraction of the sheath 144 may be used to selectively control the length of the needle distal tip 54. As shown, the needle distal tip 54 is in a configuration distally extended from the distal end 146 of the retracted sheath 144.

The insulating sheath 140 may be formed from one or more suitable insulating material such as polyester shrink tubing, and parylene coating such as parylene C. Generally, the length of the conductive distal tip 54 ranges from about 1 to about 4 cm, usually from about 2 to about 3 cm, normally about 2 cm. In an embodiment, the conductive distal end is a T-type active electrode.

Now referring back to FIGS. 5D-E, the radio frequency energy generator 410 is configured to deliver power to the fibroid 18 at the target site 16, in a an amount ranging from about 1 to about 50 W, generally from about 10 to about 40 W, usually from about 20 to about 40 W, normally about 30 W. In an embodiment, the radio frequency energy generator 410 is configured to deliver and/or maintain a target temperature to the target site 16 ranging from about 50 to about 110° C., usually from about 60 to about 100° C., normally about 90° C.

The target site 16, such as fibroid 18, generally has an initial untreated diameter greater than about 2 cm, usually from about 1 to about 6 cm, normally about 2 cm. During the treatment of the fibroid 18, the needle 14 may be inserted one or more times into the tissue as may be necessary. In an embodiment, the needle distal tip 54, may be deployed into the tissue, up to 3 cm as measured from the distal end of the of the delivery device 10. During the treatment, the deployed length of the needle penetrating the tissue is visualized through the ultrasound imaging system 500.

By way of operation, in an embodiment, the deflectable distal tip 26 of the rigid shaft 24 may be deflected by the use of pull or tensioning wire(s) housed within the shaft 24. In another embodiment, the distal tip may have pre-determined deflection as compared to a longitudinal axis at a proximal portion of the device. Deflection may occur at a true mechanical pivot or at a flexible zone at the shaft distal end. When the delivery shaft 24 is deflectable by a user, various needles 14 may be used to match the amount of deflection provided by the distal tip 26 as well as the amount of tilt provided by the ultrasound array 80. Hence, the needle guide 58 may be empty until the distal end 26 of the shaft 24 is deflected. For example, the shaft 24 may be inserted in a straight configuration. The distal tip 26 may then be deflected until a target anatomy is identified. A needle 14 is then back loaded within the guide passage 70 that corresponds to the amount of the deflection. Alternatively, the needle may be pre-loaded in the shaft to provide a sterile and convenient delivery device to the user.

In exemplary embodiments, the therapeutic needle 14 advancement from the guide 58 via needle advancement portion on the shaft handle 40 can be viewed in the ultrasound system 500 in real time as it is penetrated into the uterine fibroid 18 inside the uterus 17. The therapeutic needle 14 may be penetrated in several configurations (e.g., lateral, side, axially extending) depending on the ultrasound viewing angle. Advantageously, tilting of the ultrasound array 80 and angling of the distal tip 26 allows a treating physician to image most or all of the cornua and fundus of the uterus 17 with a single device 10.

Now referring back to the previous Figures, Table I below illustrates possible viewing angles κ that may be achieved by the cumulative effects of the shaft bending angle β (e.g., either through active deflection of the distal tip or a pre-shaped or pre-bent distal tip) and the ultrasound tilting angle α. The matching needle angles θ based on the possible viewing angles κ are further illustrated. In example 1, the shaft 24 is in a straight configuration so that the viewing angle κ is provided solely by the tilting angle α of the ultrasound array 80. In example 4, the needle 14 will have a straight configuration. In example 5, a non-tilted and non-bent ultrasound array 80 version is covered. It will be appreciated that the viewing angle κ will be more than the bend angle β of the shaft 24 due to the additive effect of the tilting angle α of the ultrasound array 80. This allows the bend on the distal tip 28 of the shaft 24 to be shallower without compromising the cumulative viewing angle κ, which is of particular benefit for patient insertion considerations. In the case of a deflectable distal tip 28 in which insertion may be implemented in a straight configuration, the tiled ultrasound angle α still aids in reducing the needle angle θ.

TABLE I

| Example | Viewing Angle (κ) | Tilt Angle (α) | Bend Angle (β) | Needle Angle (θ) |
|---|---|---|---|---|
| 1 | 7°-10° | 7°-10° | 0° | 80° |
| 2 | 20° | 7°-10° | 10°-13° | 70° |
| 3 | 45° | 7°-10° | 35°-38° | 45° |
| 4 | 90° | 7°-10° | 80°-83° | 0° |
| 5 | 0° | 0° | 0° | 90° |

Figure 10A:
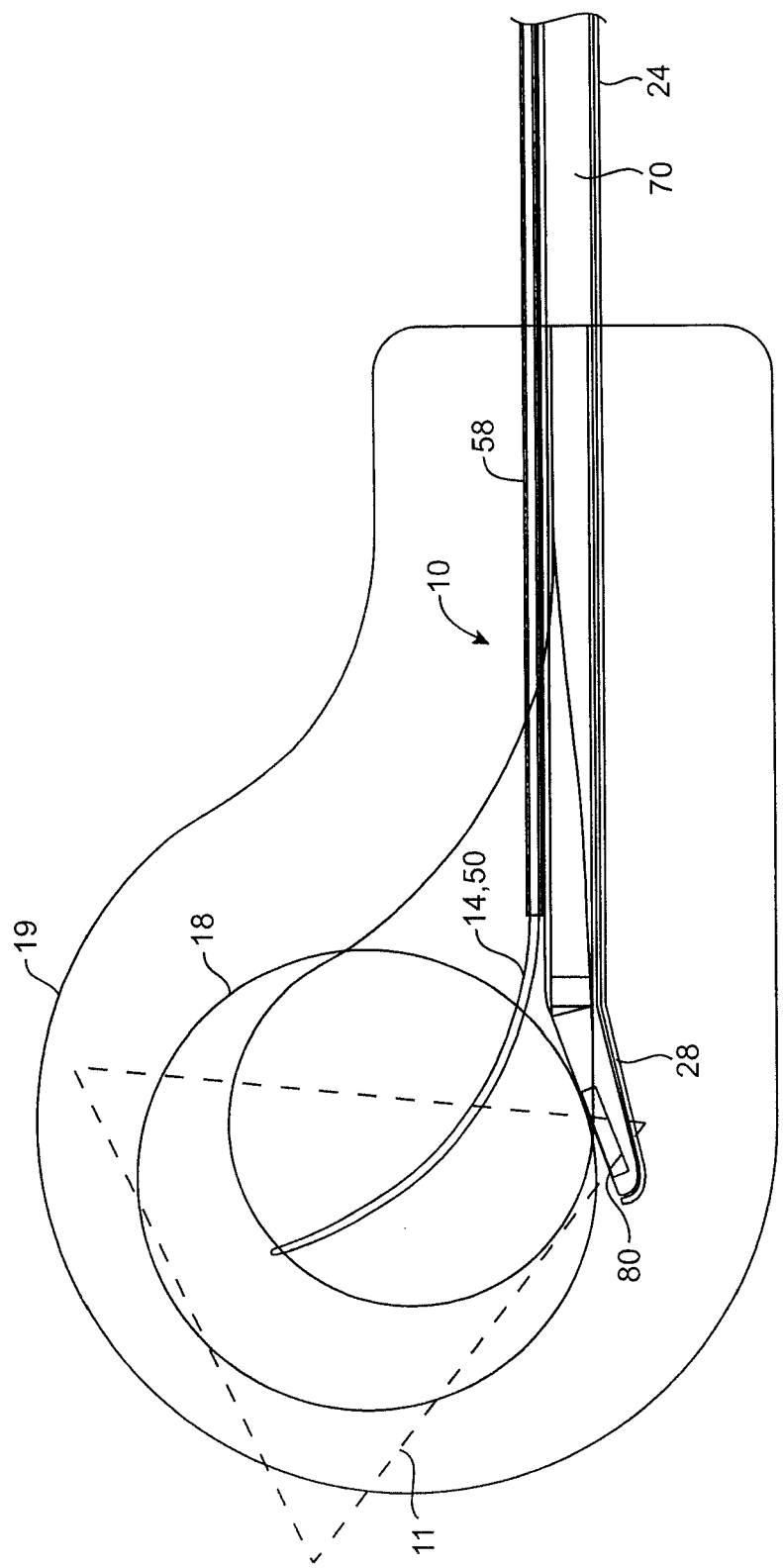
FIGS. 10A through 10C illustrate use of the system of FIG. 1A within a uterus for the treatment of fibroids in accordance with the principles of the present invention.
Figure 10B:
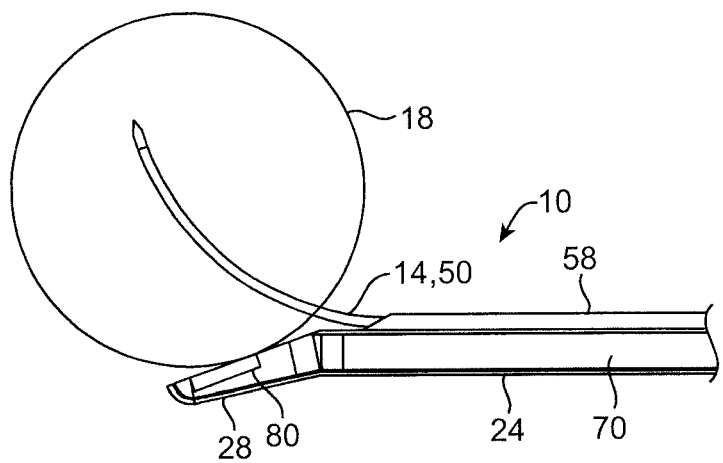
Figure 10C:
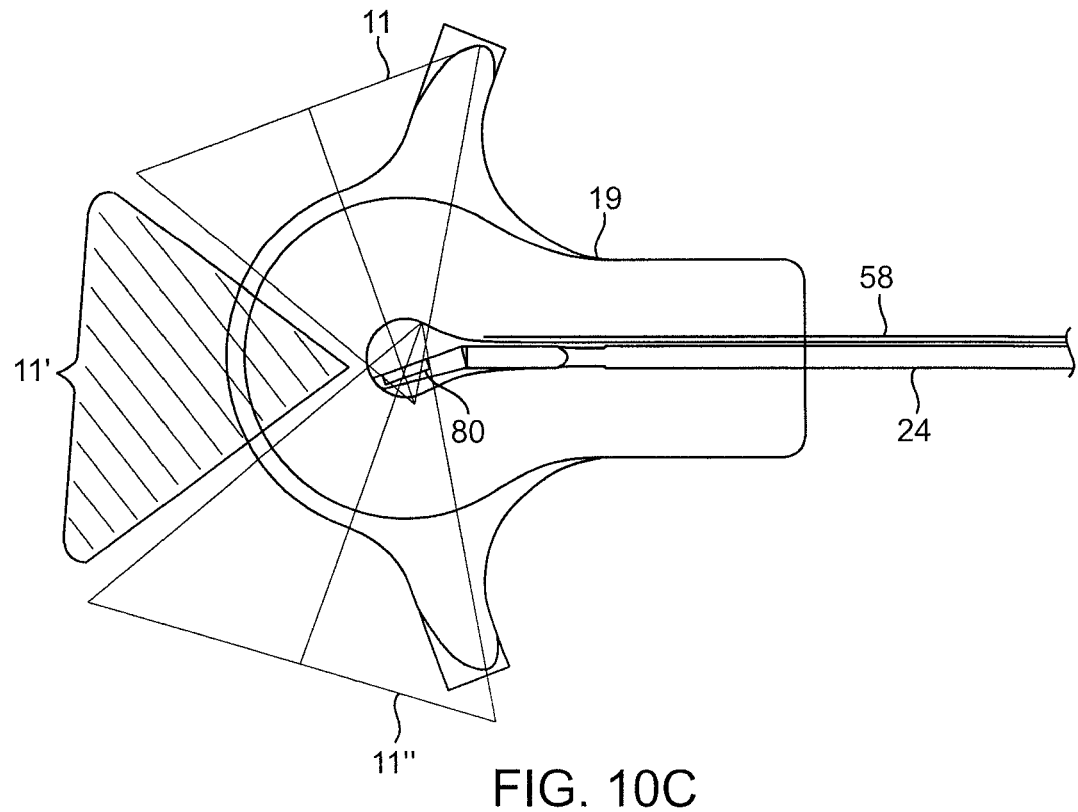

Referring now to FIGS. 10A and 10C, a method, embodying features of the present invention, for using the system 10 of FIG. 1A to treat fibroids or tumors 18 within the uterus 19 is illustrated. Typically, the rigid shaft 24 is inserted in a straight configuration within the uterus 19. The distal tip 28 of the rigid shaft 24 may then be selectively deflected by a pull wire. The ultrasound imaging insert 70 may then be loaded within the axial passage 32 of the shaft 24 prior to, concurrent with, or subsequent to shaft 24 insertion, wherein a distal portion of the insert 70 conforms to the deflected shaft distal end 28. Loading may further involve axially or rotationally aligning the ultrasound imaging insert 70 within the rigid shaft 24. A needle angle θ is then selected by the physician from a plurality of needles 14 having different curvatures based on the shaft bending angle β and the ultrasound tilting angle α. The selected curved needle 14 is then loaded within the passage 59 of the needle guide 58.

In exemplary embodiments, the therapeutic needle 14 advancement from the guide 58 via needle advancement button on the shaft handle 40 can be viewed in real time as it is penetrated into the uterine fibroid 18 inside the uterus 19 as illustrated by the viewing plane 11 in FIGS. 10A and 10B. The therapeutic needle 14 may be penetrated in several configurations (e.g., lateral, side, axially extending) depending on the ultrasound viewing angle κ. Advantageously, tilting of the ultrasound array 80 and angling of the distal tip 28 allows a treating physician to image most or all of the cornua and fundus of the uterus 19 with a single device 10. As shown in FIG. 10C, the device 10 may be configured so as to provide the desired viewing angle κ (e.g., distally forward direction, side-viewing or lateral direction). It will further be appreciated that manipulation of the device 10, as for example, torquing and/or rotating the rigid device 16 in addition to tip deflection β and ultrasound tilt α will allow a physician to obtain the desired viewing planes 11, 11', 11". For example, viewing plane 11" may be achieved if the device 10 was rotated 180° about its axis. Further, viewing plane 11' may be achieved by torquing the device 10.

Although certain exemplary embodiments and methods have been described in some detail, for clarity of understanding and by way of example, it will be apparent from the foregoing disclosure to those skilled in the art, that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A rigid delivery system comprising:
   a rigid shaft having a proximal end, a distal end, a longitudinal axis, and a passage therethrough, wherein the passage has a distal end with an alignment feature on an inner surface thereof; and
   an ultrasound imaging insert removably disposed within the passage and having an ultrasound array and an outer engaging surface which is asymmetrically inclined relative to the longitudinal axis and rotationally aligns with the alignment feature on the inner surface of the passage by contacting the inner surface when the insert is fully received in the passage of the shaft, wherein the ultrasound array has a field of view with a center line which is tilted in a distally forward direction relative to the longitudinal axis and wherein the imaging insert may be removed and reused.

2. A system as in claim 1, wherein the alignment feature comprises a flat viewing surface which permits imaging with the ultrasound array of the imaging insert.

3. A system as in claim 1, further comprising a needle deployable from the rigid shaft.

4. A system as in claim 3, wherein the needle is deployable within the field of the ultrasound array.

5. A system as in claim 4, wherein the needle is straight when carried in the rigid shaft and curves as it is deployed.

6. A system as in claim 3, wherein the needle comprises an electrode.

7. A system as in claim 3, wherein the needle is adapted to deliver an agent to a fibroid.

8. A system as in claim 1 wherein said alignment feature comprises a mechanical alignment means.

9. A system as in claim 1 wherein said alignment feature provides for axial or rotational alignment.

\* \* \* \* \*